(12) United States Patent
Weisbart

(10) Patent No.: US 9,155,801 B2
(45) Date of Patent: Oct. 13, 2015

(54) AMINO ACID SEQUENCES WHICH ENHANCE PEPTIDE CONJUGATE SOLUBILITY

(75) Inventor: Richard H. Weisbart, Los Angeles, CA (US)

(73) Assignee: The United States Government as Represented by the Department of Veterans Affairs, Washington, DC (US)

( * ) Notice: Subject to any disclaimer, the term of this patent is extended or adjusted under 35 U.S.C. 154(b) by 47 days.

(21) Appl. No.: 13/322,914

(22) PCT Filed: May 27, 2010

(86) PCT No.: PCT/US2010/036482
§ 371 (c)(1),
(2), (4) Date: Nov. 28, 2011

(87) PCT Pub. No.: WO2010/138769
PCT Pub. Date: Dec. 2, 2010

(65) Prior Publication Data
US 2012/0070875 A1   Mar. 22, 2012

Related U.S. Application Data

(60) Provisional application No. 61/182,030, filed on May 28, 2009.

(51) Int. Cl.
*A61K 47/48*   (2006.01)
*C07K 16/44*   (2006.01)
*C12N 15/62*   (2006.01)

(52) U.S. Cl.
CPC ..... *A61K 47/48538* (2013.01); *A61K 47/48415* (2013.01); *C07K 16/44* (2013.01); *C12N 15/625* (2013.01); *C07K 2317/77* (2013.01); *C07K 2319/02* (2013.01); *C07K 2319/036* (2013.01); *C07K 2319/21* (2013.01); *C07K 2319/41* (2013.01)

(58) Field of Classification Search
None
See application file for complete search history.

(56) References Cited

U.S. PATENT DOCUMENTS

2010/0055715 A1   3/2010   Pearce et al.
2010/0143358 A1   6/2010   Weisbart

FOREIGN PATENT DOCUMENTS

| WO | WO 01/16182 A2 | 3/2001 |
|---|---|---|
| WO | WO 03/033515 A1 | 4/2003 |
| WO | WO 03/070747 A2 | 8/2003 |
| WO | WO 03/106498 A2 | 12/2003 |
| WO | WO 2004/055042 A1 | 7/2004 |
| WO | WO 2004/106503 A1 | 12/2004 |
| WO | WO 2006/017853 A2 | 2/2006 |
| WO | WO 2007/084342 A2 | 7/2007 |

OTHER PUBLICATIONS

Daly et al. Expression of heterologous proteins in *Pichia pastoris*: a useful experimental tool in protein engineering and production. J Mol Recognit. Mar.-Apr. 2005;18(2):119-38.*
Daugherty et al. Formulation and delivery issues for monoclonal antibody therapeutics. Adv Drug Deliv Rev. Aug. 7, 2006;58(5-6):686-706. Epub May 22, 2006.*
AZE89399, GENESEQ™ database, Thomson Reuters, Philadelphia, USA, Accession No. AZE89399, Mar. 17, 2011.*
AZH14115, GENESEQ™ database, Thomson Reuters, Philadelphia, USA, Accession No. AZH14115, May 26, 2011.*
Guo et al. Protein tolerance to random amino acid change. Proc Natl Acad Sci U S A. Jun. 22, 2004;101(25):9205-10.*
MacCallum et al. Antibody-antigen interactions: contact analysis and binding site topography. J Mol Biol. Oct. 11, 1996;262(5):732-45.*
Wu et al. Humanization of a murine monoclonal antibody by simultaneous optimization of framework and CDR residues. J Mol Biol. Nov. 19, 1999;294(1):151-62.*
Bamford et al., "The 5' untranslated region, signal peptide, and the coding sequence of the carboxyl terminus of IL-15 participate in its multifaceted translational control", *J. Immunol.*, 160(9):4418-26 (1998).
Hansen et al., "Antibody-mediated Hsp70 protein therapy", *Brain Res.*, 1088(1):187-96 (2006).
Onu et al., "Regulation of IL-15 secretion via the leader peptide of two IL-15 isoforms", *J. Immunol.*, 158(1):255-62 (1997).
Aucher et al., "Differences in Mesentericin Secretion Systems from two *Leuconostoc* Strains," *FEMS Microbiol. Lett.* (2004), 232:15-22, Elsevier B.V.
Heinrich et al., "Biological Activity of the Growth Factor-Induced Cytokine N51: Structure-Function Analysis Using N51/Interleukin-8 Chimeric Molecules," *Mol. Cell. Biol.* (1994), 14(5):2849-2861, American Society for Microbiology.

* cited by examiner

*Primary Examiner* — David Romeo
(74) *Attorney, Agent, or Firm* — DLA Piper LLP (US)

(57) ABSTRACT

The present invention provides peptide conjugates having improved solubility as well as increased secretion during cell based production, as well as methods of utilizing such peptides. The peptide conjugates include a short peptide domain defined by the amino acid sequence AGIH (SEQ ID NO: 8) and may include a biologically active molecule useful in intracellular and intranuclear transport of the biologically active molecule to treat various disorders and diseases.

14 Claims, 2 Drawing Sheets

```
        FR1
         E  V  Q  L  V  E  S  G  G  G  L  V  K  P  G  G  S  R
3E10 GAGGTGCAGCTGGTGGAGTCTGGGGGAGGCTTAGTGAAGCCTGGAGGGTCCCGG

CDR1
         K  L  S  C  A  A  S  G  F  T  F  S  D  Y  G  M  H
3E10 AAACTCTCCTGTGCAGCCTCTGGATTCACTTTCAGT GACTATGGAATGCAC

FR2
         W  V  R  Q  A  P  E  K  G  L  E  W  V  A
3E10 TGGGTCCGTCAGGCTCCAGAGAAGGGGCTGGAGTGGGTTGCA

CDR2
         Y  I  S  S  G  S  S  T  I  Y  Y  A  D  P  V  K  G
3E10 TACATTAGTAGTGGCAGTAGTACCATCTACTATGCAGACACAGTGAAGGGC

FR3
         R  F  T  I  S  R  D  N  A  K  N  T  L  F  L  Q  M  T
3E10 CGATTCACCATCTCCAGAGACAATGCCAAGAACACCCTGTTCCTGCAAATGACC

S  L  R  S  E  D  T  A  M  Y  Y  C  A  R
3E10 AGTCTAAGGTCTGAGGACACAGCCATGTATTACTGTGCAAGG

CDR3                          FR4
         R  G  L  L  L  D  Y        W  G  Q  G  T  T  L  T  V  S  S
3E10 CGGGGGTTACTACTTGACTAC       TGGGGCCAAGGCACCACTCTCACAGTCTCCTCA
```

FIG. 1

```
              FR1
              D   I   V   L   T   Q   S   P   A   S   L   A   V   S   L   G   Q   R
3E10VkIII     GACATTGTGCTGACACAGTCTCCTGCTTCCTTAGCTGTATCTCTGGGGCAGAGG

S   I   V   M   T   Q   T   P   K   F   L   P   V   S   A   G   D   R
3E10VkSER     AGTATTGTGATGACCCAGACTCCCAAATTCCTGCTTGTATCAGCAGGAGACAGG

CDR1
              A   T   I   S   C   R   A   S   K   S   V   S   T   S   S   Y   S   Y   M   H
3E10VkIII     GCCACCATCTCCTGC     AGGGCCAGCAAAAGTGTCAGTACATCTAGCTATAGTTACATGCAC

V   T   M   T   C   K   A   S   Q   S   V   G   N   N   V   A
3E10VkSER     GTCACCATGACCTGC     AAGGCCAGTCAGAGTGTGGGTAATAATGTAGCC

FR2
              W   Y   Q   Q   K   P   G   Q   P   P   K   L   L   I   K
3E10VkIII     TGGTACCAACAGAAACCAGGACAGCCACCCAAACTCCTCATCAAG

W   Y   Q   Q   K   P   G   Q   S   P   K   L   L   I   Y
3E10VkSER     TGGTACCAACAGAAGCCAGGACAGTCTCCTAAACTGCTGATATAC
              CDR2                              FR3
              Y   A   S   Y   L   E   S           G   V   P   A   R   F   S   G   S   G
3E10VkIII     TATGCATCCTACCTAGAATCT               GGGGTTCCTGCCAGGTTCAGTGGCAGTGGG

Y   A   S   N   R   Y   T           G   V   P   D   R   F   T   G   S   G
3E10VkSER     TATGCATCCAATCGCTACACT               GGAGTCCCTGATCGCTTCACTGGCAGTGGA

S   G   T   D   F   T   L   N   I   H   P   V   E   E   E   D   A   A
3E10VkIII     TCTGGGACAGACTTTCACCTCAACATCCATCCTGTGGAGGAGGAGGATGCTGCA

S   G   T   D   F   T   F   T   I   S   S   V   Q   V   E   D   L   A
3E10VkSER     TCTGGGACAGATTTCACTTTCACCATCAGCAGTGTGCAGGTTGAAGACCTGGCA

CDR3                                          FR4
              T   Y   Y   C   Q   Q   S   R   E   F   P   W   T           F   G   G   G
3E10VkIII     ACATATTACTGT        CAGCACAGTAGGGAGTTCCCGTGGACG              TTCGGTGGAGGC

V   Y   F   C   Q   Q   H   Y   S   S   P   N   T           F   G   G   G
3E10VkSER     GTTTATTTCTGT        CAGCAGCATTATAGCTCTCCGTGGACG              TTCGGTGGAGGC

T   K   L   E   L   K
3E10VkIII     ACCAAGCTGGAGTTGAAA

T   K   L   E   I   K
3E10VkSER     ACCAAGCTGGAAATCAAA
```

FIG. 2

SEQUENCE LISTING

```
<160> NUMBER OF SEQ ID NOS: 12

<210> SEQ ID NO 1
<211> LENGTH: 348
<212> TYPE: DNA
<213> ORGANISM: Mus musculus

<400> SEQUENCE: 1
gaggtgcagc tggtggagtc tgggggaggc ttagtgaagc ctggagggtc ccggaaactc      60
tcctgtgcag cctctggatt cactttcagt gactatggaa tgcactgggt ccgtcaggct     120
ccagagaagg ggctggagtg ggttgcatac attagtagtg gcagtagtac catctactat     180
gcagacacag tgaagggccg attcaccatc tccagagaca atgccaagaa caccctgttc     240
ctgcaaatga ccagtctaag gtctgaggac acagccatgt attactgtgc aaggcggggg     300
ttactacttg actactgggg ccaaggcacc actctcacag tctcctca                 348
```

<210> SEQ ID NO 2
<211> LENGTH: 116
<212> TYPE: PRT
<213> ORGANISM: Mus musculus

<400> SEQUENCE: 2

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 3
<211> LENGTH: 333
<212> TYPE: DNA
<213> ORGANISM: Mus musculus

<400> SEQUENCE: 3
gacattgtgc tgacacagtc tcctgcttcc ttagctgtat ctctggggca gagggccacc      60
atctcctgca gggccagcaa aagtgtcagt acatctagct atagttacat gcactggtac     120
caacagaaac caggacagcc acccaaactc ctcatcaagt atgcatccta cctagaatct     180
ggggttcctg ccaggttcag tggcagtggg tctgggacag actttcacct caacatccat     240
cctgtggagg aggaggatgc tgcaacatat tactgtcagc acagtaggga gtttccgtgg     300
acgttcggtg gaggcaccaa gctggagttg aaa                                  333

<210> SEQ ID NO 4
<211> LENGTH: 111
<212> TYPE: PRT
<213> ORGANISM: Mus musculus

<400> SEQUENCE: 4

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110

<210> SEQ ID NO 5
<211> LENGTH: 321
<212> TYPE: DNA
<213> ORGANISM: Mus musculus

<400> SEQUENCE: 5

```
agtattgtga tgacccagac tcccaaattc ctgcctgtat cagcaggaga cagggttacc    60
atgacctgca aggccagtca gagtgtgggt aataatgtag cctggtacca acagaagcca   120
ggacagtctc ctaaactgct gatatactat gcatccaatc gctacactgg agtccctgat   180
cgcttcactg gcagtggatc tgggacagat ttcactttca ccatcagcag tgtgcaggtt   240
gaagacctgg cagtttattt ctgtcagcag cattatagct ctccgtggac gttcggtgga   300
ggcaccaagc tggaaatcaa a                                             321
```

<210> SEQ ID NO 6
<211> LENGTH: 107
<212> TYPE: PRT
<213> ORGANISM: Mus musculus

<400> SEQUENCE: 6

Ser Ile Val Met Thr Gln Thr Pro Lys Phe Leu Pro Val Ser Ala Gly
1               5                   10                  15

Asp Arg Val Thr Met Thr Cys Lys Ala Ser Gln Ser Val Gly Asn Asn
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Trp
                85                  90                  95

Thr Phe Gly Gly Gly Thr Lys Leu Glu Ile Lys
            100                 105

<210> SEQ ID NO 7
<211> LENGTH: 12
<212> TYPE: DNA
<213> ORGANISM: Artificial Sequence
<220> FEATURE:
<223> OTHER INFORMATION: Synthetic construct: codon sequence of SEQ ID
      NO:8
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 7
gcnggnathc ay                                                        12

<210> SEQ ID NO 8

```
<211> LENGTH: 4
<212> TYPE: PRT
<213> ORGANISM: Artificial Sequence
<220> FEATURE:
<223> OTHER INFORMATION: Synthetic construct

<400> SEQUENCE: 8

Ala Gly Ile His
1

<210> SEQ ID NO 9
<211> LENGTH: 6
<212> TYPE: PRT
<213> ORGANISM: Artificial Sequence
<220> FEATURE:
<223> OTHER INFORMATION: Synthetic construct

<400> SEQUENCE: 9

His His His His His His
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Gly Gly Gly Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Gly Phe Pro Arg Gly Phe Pro Ala Gly Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Thr Arg His Arg Gln Pro Arg Gly Trp Glu Gln Leu
1               5                   10
```

AMINO ACID SEQUENCES WHICH ENHANCE PEPTIDE CONJUGATE SOLUBILITY

CROSS REFERENCE TO RELATED APPLICATIONS

This application is a 35 USC §371 National Stage application of International Application No. PCT/US2010/036482 filed May 27, 2010; which claims the benefit under 35 USC §119(e) to U.S. Application Ser. No. 61/182,030 filed May 28, 2009. The disclosure of each of the prior applications is considered part of and is incorporated by reference in the disclosure of this application.

GRANT INFORMATION

This work was supported by the U.S. Department of Veterans Affairs, and the Federal Government has certain rights in this invention.

BACKGROUND OF THE INVENTION

1. Field of the Invention

The present invention relates generally to conjugate molecules and more specifically, to conjugate molecules and their use in the delivery of biologically active agents into cells.

2. Background Information

Various delivery vehicles have been used to deliver biologically active molecules (e.g., peptides) into cells for therapeutic or diagnostic purposes. Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the third alpha helix of *Drosophila* Antennapedia (Ante) homeotic transcription factor. The small protein transduction domains (PTDs) from these proteins can be incorporated into peptide conjugates including a biologically active molecule to transport the conjugate into a cell. The potential disadvantage of these vectors is that they are foreign proteins that may be immunogenic in humans.

Certain anti-DNA autoantibodies have also been shown to penetrate cells and localize to the cell nucleus. Cellular penetration by anti-DNA antibodies was initially demonstrated in peripheral blood T-lymphocytes and, subsequently, was shown to affect their function. This phenomenon has allowed the use of certain antibodies in the generation of peptide conjugates capable of transporting a wide variety of biologically active materials, e.g., nuclear transcription factors, enzymes, enzyme inhibitors, genes, and the like, to the cell nucleus for a variety of therapeutic effects. Any variety of agents may be transported via conjugation to the antibody, or fragment of the antibody, such as inorganic and organic molecules, pharmaceutical agents, drugs, peptides, proteins, genetic material, and the like.

A particular class of monoclonal antibodies that is known to be utilized to transport a wide variety of biologically important molecules into target cells, such as kidney cells, brain cells, ovarian cells, bone cells, and the like is mAb 3E10 and mutants and/or functional fragments thereof. Monoclonal antibody 3E10 is produced by a hybridoma 3E10 placed permanently on deposit with the American Type Culture Collection, 10801 University Blvd., Manassas, Va. 20110-2209, USA, on Aug. 31, 2000, according to the terms of the Budapest Treaty under ATCC accession number PTA-2439. mAb 3E10 (or functional fragments thereof) can be conjugated to the biological molecule of interest to form an antibody conjugate that is capable of being transported into the cell. Upon entry into the cell, the antibody conjugate localizes in and around the cell nucleus. Such antibody conjugates may be used in the same manner as other conjugated delivery systems where an antibody or other targeting vehicle is conjugated to the biological molecule of interest to provide delivery to desired cells in the in vivo or in vitro environment.

The anti-DNA antibody fragment 3E10 Fv has been demonstrated to be an ideal molecular delivery vehicle due to its efficiency in penetrating into living cells with specific nuclear localization, absence of toxicity, and successful delivery of therapeutic cargo proteins in vitro and in vivo. Although antibodies that penetrate living cells are frequently toxic or injurious and may explain some of the pathologic manifestations of the autoimmune diseases in which they are found, antibody mAb 3E10, in contrast, shows no harm to cells that it penetrates in tissue culture. Moreover, studies in vitro have shown that mAb 3E10 and scFv fragments of mAb 3E10 can transport relatively large proteins, such as catalase, into the nucleus of cells in tissue culture. Moreover, mAb 3E10 or fragments thereof (e.g., Fv) should not generate significant inflammation in vivo which could hinder therapeutic efficacy of a biologically active molecule conjugated thereto.

It is well known that transporter proteins are involved in the cellular uptake of various molecules into and/or through cells. Carrier-mediated transport systems use proteins that are anchored to the cell membrane, typically by a plurality of membrane-spanning domains and function by transporting their substrates via active or passive mechanisms. Carrier-mediated transport systems are involved in the active or non-active, facilitated transport of many important nutrients such as vitamins, sugars, and amino acids. Carrier-mediated transporters are also present in organs such as the liver and kidney, in which the proteins are involved in the excretion or re-absorption of circulating compounds. Polar or hydrophilic compounds typically diffuse poorly across the lipid bilayers that constitute cellular membranes. For many small molecules (e.g., amino acids, di- and tripeptides, monosaccharides, nucleosides and water-soluble vitamins) there exist specific carrier-mediated transporters for active transport of the solute molecules across biological membranes.

The pathways that allow various molecules to cross cell membranes have been determined. For example, 3E10 Fv is transported by a nucleoside transport pathway allowing it to penetrate cells and localize into the nucleus as discussed in U.S. patent application Ser. No. 12/126,810, filed May 23, 2008; incorporated herein by reference in its entirety.

While various peptides, such as mAb 3E10 Fv have been developed as an intracellular and intranuclear transport vehicle, it has been difficult to produce large amounts of these peptides while maintaining its solubility.

SUMMARY OF THE INVENTION

The present invention is based on the seminal discovery of a short peptide domain defined by four amino acids that greatly increases solubility of conjugated molecules. The short peptide domain defined by the amino acid sequence AGIH (SEQ ID NO: 8) may be used to generate peptide-biologically active molecule conjugates having improved solubility as well as increased secretion of the peptide conjugate during cell based production.

Accordingly, in one embodiment, the present invention provides an isolated peptide with a core amino acid sequence AGIH (SEQ ID NO: 8).

In another embodiment, the present invention provides a peptide-biologically active molecule conjugate. The conjugate includes a peptide with the amino acid sequence AGIH (SEQ ID NO: 8), and a biologically active molecule. In various embodiments, the biologically active molecule is a protein or a nucleic acid molecule. In illustrative examples, the biologically active molecule is a protein. For example, the biologically active molecule may be an antibody, an antibody fragment, an enzyme, a transcription factor, an siRNA molecule, a DNA molecule, an RNA molecule, an siRNA-protein conjugate, an siRNA-peptide conjugate, and siRNA-antibody conjugate.

In various embodiments where the biologically active molecule is a protein, the peptide is conjugated to the N-terminus of the protein. Alternatively, in embodiments where the biologically active molecule is a nucleic acid molecule, the peptide is conjugated to the 5' or 3' end of the nucleic acid molecule. In various embodiments, the peptide is conjugated to the biologically active molecule by a linker molecule.

In another embodiment, the present invention provides a peptide-antibody conjugate. The conjugate includes a peptide including the amino acid sequence AGIH (SEQ ID NO: 8), and an antibody, variant thereof, or functional fragment thereof having a binding specificity of an antibody as produced by a hybridoma having ATCC accession number PTA 2439, wherein the peptide is conjugated to the N-terminus of the antibody, variant thereof, or functional fragment thereof. In one embodiment, the antibody of the conjugate is mAb 3E10 as produced by the hybridoma having ATCC accession number PTA 2439. In various embodiments, the antibody or variant thereof has a light chain having an amino acid sequence at least 95% identical to the amino acid sequence of 3E10VκIII (SEQ ID NO: 4) set forth in FIG. 2 and/or a heavy chain having an amino acid sequence at least 95% identical to the amino acid sequence SEQ ID NO: 2 set forth in FIG. 1. On one embodiment, the antibody is a humanized variant of an antibody produced by the hybridoma having ATCC accession number PTA 2439. In some embodiments, the functional fragment is a Fab, F(ab')$_2$, Fv, or single chain Fv (scFv) fragment. In some embodiments, the functional fragment includes the variable region of the heavy chain (VH) and variable region of the kappa light chain (Vκ) of mAb 3E10.

In another embodiment, the present invention provides a peptide-antibody conjugate. The conjugate includes a peptide including the amino acid sequence AGIH (SEQ ID NO: 8), and an antibody comprising a light chain having an amino acid sequence at least 95% identical to the amino acid sequence of 3E10VκIII (SEQ ID NO: 4) set forth in FIG. 2 and a heavy chain having an amino acid sequence at least 95% identical to the amino acid sequence SEQ ID NO: 2 set forth in FIG. 1, a variant thereof, or functional fragment thereof, wherein the peptide is conjugated to the N-terminus of the antibody, variant thereof, or functional fragment thereof.

In various aspects, the peptide-antibody conjugate further includes a biologically active molecule. The peptide-antibody conjugate may be joined to the biologically active molecule by a linker molecule.

In another embodiment, the present invention provides an isolated nucleic acid encoding any of the peptide conjugates of the present invention.

In another embodiment, the present invention provides a pharmaceutical composition including any of the peptide conjugates of the present invention optionally combined with a pharmaceutically acceptable carrier.

In yet another embodiment, the present invention provides a method of increasing the solubility of a biologically active molecule. The method includes conjugating a peptide comprising the amino acid sequence AGIH (SEQ ID NO: 8) to the biologically active molecule, wherein when the biologically active molecule is a protein, the peptide is conjugated to the N-terminus of the protein.

In yet another embodiment, the present invention provides a method of producing a protein. The method includes transforming a host cell with an expression construct, and culturing the host cell under conditions suitable for producing the conjugate. In various embodiments, the expression construct includes a nucleic acid molecule encoding a protein conjugate including a protein and a peptide, wherein the peptide includes of the amino acid sequence AGIH (SEQ ID NO: 8) and is conjugated to the N-terminus of the protein. In some embodiments, the host cell is a *Pichia pastoris* or *E. coli* cell.

BRIEF DESCRIPTION OF THE DRAWINGS

FIG. 1 shows the nucleotide sequence (SEQ ID NO: 1; GenBank Accession NO. L16982) and amino acid sequence (SEQ ID NO: 2) of mAb 3E10 VH.

FIG. 2 shows the nucleotide and amino acid sequences of mAb 3E10 Vκ light chains, 3E10VκIII (GenBank Accession No. L34051; SEQ ID NOs: 3 and 4, for nucleotide and amino acid sequences, respectively) and 3E10VκSER (GenBank Accession No. L16981; SEQ ID NOs: 5 and 6, for nucleotide and amino acid sequences, respectively).

DETAILED DESCRIPTION OF THE INVENTION

The present invention is based on the seminal discovery of a short peptide domain defined by a core of four amino acids that greatly increases solubility and/or secretion of a conjugated protein. The short peptide domain defined by the amino acid sequence AGIH (SEQ ID NO: 8) may be used to generate peptide-biologically active molecule conjugates that exhibit improved solubility as well as increased secretion of the peptide conjugate during cell based production.

Before the present methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs.

In accordance with the present invention, there are provided conjugates including a peptide including the amino acid sequence AGIH (SEQ ID NO: 8) and a biologically-active molecule. The peptide increases the solubility of the conjugate. In various embodiments, the conjugates may be used to transport a biologically active molecule into a cell; both intracellular and/or intranuclear transport.

While the inventive core peptide AGIH is preferred, it is understood that additional amino acid residues at the amino- or carboxy-termini of AGIH, or both, are included in the invention, as long as the function of AGIH is preserved (e.g., allows for increased secretion and/or solubility of the conjugate/biologically active molecule). For example, the AGIH peptide of the invention can be as short as 4 amino acid residues in length or as long as about 50 amino acid residues in length. Thus, peptides including the minimal core of AGIH that are about 4-50 amino acid residues, 4-40, 4-30, 4-25, 4-20, 4-15, 4-10 or 4-8 amino acids in length or any variation thereof are included in the invention. It is preferred that the core AGIH peptide is not derived from the biologically active molecule to which it is conjugated (e.g., "heterologous thereto").

A "conjugate" as used herein generally refers to a molecule which contains a peptide including the core amino acid sequence AGIH (SEQ ID NO: 8) conjugated with a biologically active molecule. Typically, the conjugate is capable of being transported into a cell, for example, by a nucleoside transport pathway. The resulting conjugate including the core amino acid sequence and biologically active molecule is operably linked in a manner that preserves the biological function of the biologically active molecule.

As used herein, the phrase "biologically active molecule" refers to a molecule that has a biological effect in a cell. In certain embodiments the active molecule may be an inorganic molecule, an organic molecule, a small organic molecule, a drug compound, a peptide, a polypeptide, such as an enzyme or transcription factor, an antibody, an antibody fragment, a peptidomimetic, a lipid, a nucleic acid such as a DNA or RNA molecule, a ribozyme, hairpin RNA, siRNA (small interfering RNAs) of varying chemistries, miRNA, siRNA-protein conjugate, an siRNA-peptide conjugate, and siRNA-antibody conjugate, an antagomir, a PNA (peptide nucleic acid), an LNA (locked nucleic acids), or a morpholino. In certain illustrative embodiments, the active agent is a polypeptide or peptide.

For example, in various embodiments, the active molecule may be α-glucosidase, α-L-iduronidase, α-galactosidase A, arylsulfatase, N-acetylgalactosamine-6-sulfatase or β-galactosidase, iduronate 2-sulfatase, ceramidase, galactocerebrosidase, β-glucuronidase, Heparan N-sulfatase, N-Acetyl-α-glucosaminidase, Acetyl CoA-α-glucosaminide N-acetyl transferase, N-acetyl-glucosamine-6 sulfatase, Galactose 6-sulfatase, Arylsulfatase A, B, or C, Arylsulfatase A Cerebroside, Ganglioside, Acid βgalactosidase $G_{M1}$ Gaiglioside, Acid β-galactosidase, Hexosaminidase A, Hexosaminidase B, αx-fucosidase, α-N-Acetyl galactosaminidase, Glycoprotein Neuraminidase, Aspartylglucosamine amidase, Acid Lipase, Acid Ceramidase, Lysosomal Sphingomyelinase and other Sphingomyelinase. In certain embodiments, the active agent is dystrophin, components of dystrophin-glycoprotein complex, the laminin-α2 chain, fukutin-related protein, LARGE, fukutin, EMD, LMNA, DMPK, ZNF9, and PABPN1, Glycogen synthase, Glucose-6-phosphatase, Debranching enzyme, Transglucosidase, Myophosphorylase, Phosphorylase, Phosphofructokinase, Acid Maltase Deficiency, Carnitine Palmityl Transferase, Phosphoglycerate Kinase, or Phosphoglycerate Mutase, or a nucleic acid encoding any such proteins.

In certain embodiments, the biologically active molecule is a protein such as a heat shock protein (HSP) or a transcription factor. 3E10 Fv and Fv-fusion proteins have been shown to readily transduce across cell membranes and penetrate into cell nuclei. Further, 3E10 Fv has successfully delivered biologically active proteins such as Hsp70 and p53 into living cells. As such, one of skill in the art would understand that any transcription factor or HSP may be used with the present invention.

In various embodiments where the peptide including the amino acid sequence AGIH (SEQ ID NO: 8) is conjugated to a protein, the peptide is conjugated to the N-terminus of the protein.

In one embodiment, the present invention provides a peptide-antibody conjugate, where the peptide portion includes the amino acid sequence AGIH (SEQ ID NO: 8) and which may optionally be conjugated to a biologically active molecule to form a peptide-antibody-biologically active molecule conjugate. In various embodiments the antibody or biologically active molecule of the conjugate may be a DNA-binding autoantibody. Examples of such DNA-binding autoantibodies include an antibody having the binding specificity of the antibody as produced by the hybridoma having ATCC accession number PTA 2439, antibody mAb 3E10, and variants and/or functional fragments thereof.

In various embodiments, the conjugate includes a peptide including the amino acid sequence AGIH (SEQ ID NO: 8), and an antibody, variant thereof, or functional fragment thereof having a binding specificity of an antibody as produced by a hybridoma having ATCC accession number PTA 2439, wherein the peptide is conjugated to the N-terminus of the antibody, variant thereof, or functional fragment thereof. In related embodiments, the antibody of the conjugate is mAb 3E10 as produced by the hybridoma having ATCC accession number PTA 2439.

In various embodiments, the antibody or variant thereof has a light chain having an amino acid sequence at least 95% identical to the amino acid sequence of 3E10VκIII (SEQ ID NO: 4) set forth in FIG. 2 and/or a heavy chain having an amino acid sequence at least 95% identical to the amino acid sequence SEQ ID NO: 2 set forth in FIG. 1, a variant thereof, or functional fragment thereof, wherein the peptide is conjugated to the N-terminus of the antibody, variant thereof, or functional fragment thereof.

Although antibodies that penetrate living cells are frequently toxic or injurious and may explain some of the pathologic manifestations of the autoimmune diseases in which they are found, antibody mAb 3E10, in contrast, shows no harm to cells that it penetrates in tissue culture. Moreover, studies in vitro have shown that mAb 3E10 and scFv fragments of mAb 3E10 can transport relatively large proteins, such as catalase, into the nucleus of cells in tissue culture. Moreover, mAb 3E10 or fragments thereof (e.g., Fv) should not generate significant inflammation in vivo which could hinder therapeutic efficacy of a biologically active molecule conjugated thereto.

As used herein, "specific binding" refers to antibody binding to a predetermined antigen. Typically, the antibody binds with an affinity corresponding to a $K_D$ of about $10^{-8}$ M or less, and binds to the predetermined antigen with an affinity (as expressed by $K_D$) that is at least 10 fold less, and preferably at least 100 fold less than its affinity for binding to a non-specific antigen (e.g., BSA, casein) other than the predetermined antigen or a closely-related antigen. Alternatively, the antibody can bind with an affinity corresponding to a $K_A$ of about $10^6$ $M^{-1}$, or about $10^7 M^{-1}$, or about $10^8 M^{-1}$, or $10^9 M^{-1}$ or higher, and binds to the predetermined antigen with an affinity (as expressed by $K_A$) that is at least 10 fold higher, and preferably at least 100 fold higher than its affinity for binding to a non-specific antigen (e.g., BSA, casein) other than the predetermined antigen or a closely-related antigen. In some embodiments the antibody variant or functional fragment will have the same $K_A$ or $K_D$ as an antibody produced by the hybridoma having ATCC accession number PTA 2439. In certain embodiments, the antibody variant or functional fragment will have the same $K_A$ or $K_D$ as mAb 3E10.

The term "$k_d$" (sec$^{-1}$), as used herein, is intended to refer to the dissociation rate constant of a particular antibody-antigen interaction. This value is also referred to as the off value. The term "$K_D$" (M$^{-1}$), as used herein, is intended to refer to the dissociation equilibrium constant of a particular antibody-antigen interaction.

The term "$k_a$" (M$^{-1}$sec$^{-1}$), as used herein, is intended to refer to the association rate constant of a particular antibody-antigen interaction. The term "$K_A$" (M), as used herein, is intended to refer to the association equilibrium constant of a particular antibody-antigen interaction.

Naturally occurring antibodies are generally tetramers containing two light chains and two heavy chains. Experimentally, antibodies can be cleaved with the proteolytic enzyme papain, which causes each of the heavy chains to break, producing three separate subunits. The two units that consist of a light chain and a fragment of the heavy chain approximately equal in mass to the light chain are called the Fab fragments (i.e., the "antigen binding" fragments). The third unit, consisting of two equal segments of the heavy chain, is called the Fc fragment. The Fc fragment is typically not involved in antigen-antibody binding, but is important in later processes involved in ridding the body of the antigen.

As used herein, the phrase "functional fragments of an antibody having the binding specificity of the antibody as produced by the hybridoma having ATCC accession number PTA 2439" refers to a fragment that retains the same cell penetration characteristics and binding specificity as mAb 3E10. Thus, in certain embodiments, a functional fragment of an antibody having the binding specificity of the antibody as produced by the hybridoma having ATCC accession number PTA 2439 or antibody mAb 3E10 is used in the conjugate. In some embodiments, the functional fragment used in the conjugate is selected from the group consisting of Fab, F(ab')$_2$, Fv, and single chain Fv (scFv) fragments. In certain embodiments the functional fragment is an Fv fragments or an scFv fragment. In one example, the functional fragment includes at least the antigen-binding portion of mAb 3E10. In another example, the functional fragments is an scFv fragment including the variable region of the heavy chain (VH) and variable region of the kappa light chain (Vκ) of mAb 3E10. For increased expression in the polynucleotide from which the scFv is expressed, the nucleic acids encoding the chains of mAb E310 are placed in reverse order with the Vκc cDNA being placed 5' of VH. In addition, one or more tags known in the art, preferably peptide (e.g., myc or His$_6$ (SEQ ID NO: 9)), may be incorporated into a conjugate to facilitate in vitro purification or histological localization of the conjugate. In some embodiments, a myc tag and a His$_6$ (SEQ ID NO: 9) tag are added to the C-terminus of VH.

As readily recognized by those of skill in the art, altered antibodies (e.g., chimeric, humanized, CDR-grafted, bifunctional, antibody polypeptide dimers (i.e., an association of two polypeptide chain components of an antibody, e.g., one arm of an antibody including a heavy chain and a light chain, or an Fab fragment including VL, VH, CL and CH antibody domains, or an Fv fragment comprising a VL domain and a VH domain), single chain antibodies (e.g., an scFv (i.e., single chain Fv) fragment including a VL domain linked to a VH domain by a linker, and the like) can also be produced by methods well known in the art. Such antibodies can also be produced by hybridoma, chemical synthesis or recombinant methods described, for example, in Sambrook et al. (Molecular Cloning: A Laboratory Manual 2d Ed. (Cold Spring Harbor Laboratory, 1989); incorporated herein by reference) and Harlow and Lane (Antibodies. A Laboratory Manual (Cold Spring Harbor Laboratory 1988), which is incorporated herein by reference). Both anti-peptide and anti-conjugate antibodies can be used (see, for example, Bahouth et al., Trends Pharmacol. Sci. 12:338 (1991); Ausubel et al., Current Protocols in Molecular Biology (John Wiley and Sons, N.Y. 1989) which are incorporated herein by reference). See in particular, FIGS. 1 and 2 for specific nucleotide and amino acid sequences of the illustrative antibody of the invention designated mAb 3E10.

Antibodies may be humanized by replacing sequences of the Fv variable region which are not directly involved in antigen binding with equivalent sequences from human Fv variable regions. General reviews of humanized chimeric antibodies are provided by Morrison et al., (Science 229: 1202-1207 (1985)) and by Oi et al. (BioTechniques 4:214 (1986)). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from for example, an antibody producing hybridoma. The recombinant DNA encoding the humanized or chimeric antibody, or fragment thereof, can then be cloned into an appropriate expression vector.

Humanized antibodies can alternatively be produced by CDR substitution (U.S. Pat. No. 5,225,539; Jones, Nature 321:552-525 (1986); Verhoeyan et al., Science 239:1534 (1988); and Beidler, J. Immunol. 141:4053-4060 (1988)). Thus, in certain embodiments, the antibody used in the conjugate is a humanized or CDR-grafted form of an antibody produced by the hybridoma having ATCC accession number PTA 2439. In other embodiments the antibody is a humanized or CDR-grafted form of antibody mAb 3E10. For example, the CDR regions can include amino acid substitutions such as 1, 2, 3, 4, 5, 6, 7, 8, 9, or 10 amino acid differences from those shown in the figures. In some instances, there are anywhere from 1-5 amino acid differences.

As used herein, reference to "variants of an antibody having the binding specificity of an antibody as produced by the hybridoma having ATCC accession number PTA 2439" includes variants retaining the same cell penetration characteristics and binding specificity as mAb 3E10, as well as variants modified by mutation to improve the utility thereof (e.g., improved ability to target specific cell types, improved ability to penetrate the cell membrane, improved ability to localize to the cellular DNA, and the like). Such variants include those wherein one or more conservative substitutions are introduced into the heavy chain, the light chain and/or the constant region(s) of the antibody. In some embodiments the variant has a light chain having an amino acid sequence at least 80% or at least 90% or at least 95% identical to the amino acid sequence set forth in SEQ ID NO: 4. In other embodiments, the variant has a heavy chain having an amino acid sequence at least 80% or at least 90% or at least 95% identical to the amino acid sequence set forth in SEQ ID NO: 2. Further, the invention includes antibodies that are encoded by nucleic acid sequences that hybridize under stringent conditions to the 3E10 variable region coding sequence (e.g., SEQ ID NO: 1 and/or SEQ ID NO: 3) or encode amino acid sequences at least 80% or at least 90% or at least 95% identical to the amino acid sequence set forth in SEQ ID NO: 2 or SEQ ID NO: 4.

Such variants include those wherein one or more substitutions are introduced into the heavy chain nucleotide sequence, the light chain nucleotide sequence and/or the constant region(s) of the antibody. In some embodiments the variant has a light chain having a nucleotide sequence at least 80% or at least 90% or at least 95% identical to the nucleotide sequence set forth in SEQ ID NO: 3. In other embodiments, the variant has a heavy chain having a nucleotide sequence at least 80% or at least 90% or at least 95% identical to the nucleotide sequence set forth in SEQ ID NO: 1.

One exemplary variant contemplated for use in the practice of the present invention is an mAb 3E10 VH variant involving a single change of the aspartic acid residue at position 31 to asparagine (i.e., mAb 3E10-31). The preparation of this variant and further variants and a demonstration of its cell penetration ability is described in U.S. Pat. No. 7,189,396 and incorporated by reference in its entirety. This particular mAb 3E10 variant is especially well suited for delivery of biological molecules to kidney and brain cells. Other 3E10 variants and/or functional fragments thereof may be used to provide targeting of biologically active molecules. A wide variety of variants and/or functional fragments thereof are possible provided that they exhibit substantially the same cell penetration characteristics as mAb 3E10 or mAb 3E10-31 after conjugation to a selected biologically active molecule.

In other embodiments, peptides or antibodies that target one or more specific nucleoside transporters may be generated. Such peptides or antibodies could be generated using, for example molecular modeling and protein mimetic methodologies based on structures of known substrates.

In embodiments where the conjugates include polypeptides (i.e., protein conjugates), they may be designed to place the peptide including the amino acid sequence of SEQ ID NO: 8 at the amino terminus of the conjugate using well-known recombinant DNA methodologies. Such conjugates can be expressed in a host cell as a fusion protein. Alternatively, portions of the conjugate can be chemically linked by peptide bonds or by a chemical or peptide linker molecule of various types well known in the art as discussed further herein.

As discussed herein, the present invention is based on the discovery that the addition of 4 specific amino acids to the N-terminus of mAb 3E10 Fv markedly enhanced secretion and solubility of the peptide conjugate. As such, in one embodiment, the present invention provides a method of increasing the solubility of a biologically active molecule. The method includes conjugating a peptide comprising the amino acid sequence AGIH (SEQ ID NO: 8) to the biologically active molecule, wherein when the biologically active molecule is a protein, the peptide is conjugated to the N-terminus of the protein.

In another embodiment, the present invention provides a method of producing a protein. The method includes transforming a host cell with an expression construct, and culturing the host cell under conditions suitable for producing the conjugate. In various embodiments, the expression construct includes a nucleic acid molecule encoding a protein conjugate including a protein and a peptide, wherein the peptide consists of the amino acid sequence AGIH (SEQ ID NO: 8) and is conjugated to the N-terminus of the protein.

Vectors suitable for use in preparation of proteins and/or protein conjugates include those selected from baculovirus, phage, plasmid, phagemid, cosmid, fosmid, bacterial artificial chromosome, viral DNA, Pl-based artificial chromosome, yeast plasmid, and yeast artificial chromosome. For example, the viral DNA vector can be selected from vaccinia, adenovirus, foul pox virus, pseudorabies and a derivative of SV40. Suitable bacterial vectors for use in practice of the invention methods include pQE70™, pQE60™, pQE-9™, pBLUESCRIPT™ SK, pBLUESCRIPT™ KS, pTRC99a™, pKK223-3™, pDR540™, PAC™ and pRIT2T™. Suitable eukaryotic vectors for use in practice of the invention methods include pWLNEO™, pXTI™, pSG5™, pSVK3™, pBPV™, pMSG™, and pSVLSV40™. Suitable eukaryotic vectors for use in practice of the invention methods include pWLNEO™, pXTI™, pSG5™, pSVK3™, pBPV™, pMSG™, and pSVLSV40™.

Those of skill in the art can select a suitable regulatory region to be included in such a vector, for example from lacI, lacZ, T3, T7, apt, lambda PR, PL, trp, CMV immediate early, HSV thymidine kinase, early and late SV40, retroviral LTR, and mouse metallothionein-I regulatory regions.

Host cells in which the vectors containing the polynucleotides encoding the protein conjugates can be expressed include, for example, a bacterial cell, a eukaryotic cell, a yeast cell, an insect cell, or a plant cell. For example, *E. coli, Bacillus, Streptomyces, Pichia pastoris, Salmonella typhimurium, Drosophila* S2, *Spodoptera* SJ9, CHO, COS (e.g. COS-7), or Bowes melanoma cells are all suitable host cells for use in practice of the invention methods. In exemplary embodiments, the host cell is a *Pichia pastoris* or *E. coli* cell.

Conjugates in which the biologically active molecule is a small molecule or drug compound may be generated using methods known in the art. For example, methods for attaching a drug or other small molecule pharmaceutical to protein include bifunctional chemical linkers such as N-succinimidyl (4-iodoacetyl)-aminobenzoate; sulfosuccinimidyl(4-iodoacetyl)-aminobenzoate; 4-succinimidyl-oxycarbonyl-α-(2-pyridyldithio) toluene; sulfosuccinimidyl-6-[α-methyl-α-(pyridyldithiol)-toluamido]he-xanoate; N-succinimidyl-3-(2-pyridyldithio)-proprionate; succinimidyl-6-[3(-(-2-pyridyldithio)-proprionamido]hexanoate; sulfosuccinimidyl-6-[3(-(-2-pyridyldithio)-propionamido] hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are disclosed in U.S. Pat. Nos. 5,349,066; 5,618,528; 4,569,789; 4,952,394; and 5,137,877, each of which is incorporated herein by reference in its entirety.

In certain embodiments, a conjugate of the present invention may further contain a detectable label. Such labels are known in the art and include radio-isotopes and fluorescent labels. As such, internalization of a compound evidencing passage through transporters can be detected by detecting a signal from within a cell from any of a variety of reporters. The reporter can be a label such as a fluorophore, a chromophore, a radioisotope. Confocal imagining can also be used to detect internalization of a label as it provides sufficient spatial resolution to distinguish between fluorescence on a cell surface and fluorescence within a cell; alternatively, confocal imaging can be used to track the movement of compounds over time. In another approach, internalization of a compound is detected using a reporter that is a substrate for an enzyme expressed within a cell. Once the complex is internalized, the substrate is metabolized by the enzyme and generates an optical signal or radioactive decay that is indicative of uptake. Light emission can be monitored by commercial PMT-based instruments or by CCD-based imaging systems. In addition, assay methods utilizing LCMS detection of the transported compounds or electrophysiological signals indicative of transport activity are also employed.

In some embodiments, the conjugates of the present invention may include a biologically active molecule that is a nucleic acid molecule or analog thereof. As such the conjugates may be utilized to deliver nucleic acids, or analogs thereof, to a targeted tissue or cell type. For example, protein expression can be specifically down-regulated using oligonucleotides such as, for example, antisense molecules, locked nucleic acids (LNA), peptide nucleic acids (PNA), morpholino nucleic acids and small interfering RNAs (siRNA) of various chemistries. Alternatively, expression constructs may be delivered to cells, to induce expression of a desired gene product.

Nucleic acids which modulate the expression of a certain gene or gene product may be administered. As used herein, "a nucleic acid that modulates expression of . . . " encompasses nucleic acids that up-regulate and down-regulate the expression of the given gene or gene product. For example, an expression construct can expresses the gene of interest and cause up-regulation. Alternatively, a nucleic acid that causes down-regulation can be, for example, a siRNA, a construct that expresses an antisense RNA (such as a short hairpin RNA), or a ribozyme.

Nucleic acid therapeutics, such as oligonucleotides directed against intracellular targets (mRNA or protein), are powerful therapeutic agents. Examples of oligonucleotide therapeutic agents include: antisense oligonucleotides, which are short, single-stranded DNAs and RNAs that bind to complementary mRNA and inhibit translation or induce RNaseH-mediated degradation of the transcript; siRNA oligonucleotides, which are short, double-stranded RNAs that activate the RNA interference (RNAi) pathway leading to mRNA degradation; ribozymes, which are oligonucleotide-based endonucleases that are designed to cleave specific mRNA transcripts; and nucleic acid aptamers and decoys, which are non-naturally occurring oligonucleotides that bind to and block protein targets in a manner analogous to small molecule drugs.

As used herein, the term "nucleic acid" refers to polynucleotides such as deoxyribonucleic acid (DNA), and, where appropriate, ribonucleic acid (RNA). The term should also be understood to include, as appropriate to the context or as applicable to the embodiment being described, both single-stranded polynucleotides (such as antisense) and double-stranded polynucleotides (such as siRNAs). The term "nucleic acid" encompasses, for example, DNA molecules, RNA molecules, RNAi molecules and siRNA molecules, microRNA molecules, native RNA molecules, ribozyme RNA molecules, aptamers, plasmids, cDNA molecules, antisense DNA strands, and oligonucleotides. It further encompasses DNA molecules (in the form of plasmids, cDNA, linear DNA, oligos or anti-sense DNA stands) RNA molecules (in the form of siRNA, mRNA, shRNA, ribozymes, RNAi) aptamers, proteins (antibodies, polypeptides, peptides or fragment of proteins), nucleic acids conjugated to other compounds (such as fluorescent dyes, small molecular inhibitors of specific proteins). There are a number of nucleic acid-based therapeutic agents in various stages of development at this time that are well known in the art, for example antisense agents, aptamers, ribozymes, and small interfering RNAs (siRNAs).

Antisense agents may be the most advanced class of these agents, with products such as fomivirsen, alicaforsen, oblimersen sodium, Affinitac™, and Oncomyc-NG™. Antisense agents are typically short, chemically-modified oligonucleotide chains that hybridize to a specific complementary area of a targeted mRNA. The resulting mRNA duplex is recognized and degraded by RNAse H, thereby destroying the mRNA. Because the mRNA instructions fail to reach the ribosome, production of the protein encoded by the targeted mRNA is prevented. By inhibiting the production of proteins involved in disease, antisense drugs can produce a therapeutic benefit.

An aptamer is a DNA or RNA molecule that has been selected from a random or biased pool of oligonucleic acids, based on its ability to bind to a target molecule. Aptamers can be selected which bind nucleic acids, proteins, small organic compounds and specific cell surfaces, and several have been developed which bind to proteins which are associated with disease states. Aptamers are in general more easily manufactured and are more amenable to chemical modification than are antibodies, and they can be "evolved" for tighter binding to the target by an iterative process of random modification and affinity-based selection. The evolved aptamers often have antibody-like specificities, and are therefore expected to have utility in those applications, such as therapeutics and in vitro and in vivo diagnostics, where antibodies have already proved useful, such as the product, Macugen™ (pegaptanib sodium, a PEGylated aptamer with high affinity for VEGF), for the treatment of age-related macular degeneration.

Ribozymes, or RNA enzymes, are RNA molecules that can catalyze a chemical reaction. All ribozymes found naturally so far catalyze the cleavage of RNA. They range in size from the large "hammerhead" ribozymes to the so-called "minizymes" which are synthetic constructs containing the minimal structures needed for activity. DNA-based enzymes (deoxyribozymes, or DNAzymes) having similar properties have also been prepared. The ability of ribozymes to recognize and cut specific mRNA molecules gives them considerable potential as therapeutic agents. A ribozyme designed to catalyze the cleavage of a specific mRNA would be useful as a therapeutic agent in the same way that a complimentary antisense nucleic acid would be, but with the advantage that a single ribozyme molecule can destroy many copies of the mRNA.

RNA interference (RNAi) is the phenomenon of gene-specific post-transcriptional silencing by double-stranded RNA oligomers (Elbashir et al., Nature 411: 494-498 (2001); and Caplen et al., Proc. Natl. Acad. Sci. U.S.A. 98: 9742-9747 (2001)). Small inhibitory RNAs (siRNAs), like antisense oligonucleic acids and ribozymes, have the potential to serve as therapeutic agents by reducing the expression of harmful proteins. The double-stranded siRNA is recognized by a protein complex (the RNA induced silencing complex), which strips away one of the strands, facilitates hybridization of the remaining strand to the target mRNA, and then cleaves the target strand. DNA-based vectors capable of generating siRNA within cells are also of interest for the same reason, as are short hairpin RNAs that are efficiently processed to form siRNAs within cells. siRNAs capable of specifically targeting endogenously and exogenously expressed genes have been described (see for example Paddison et al., Proc. Natl. Acad. Sci. U.S.A. 99:1443-1448 (2002); Paddison et al., Genes & Dev. 16: 948-958 (2002); Sui et al., Proc. Natl. Acad. Sci. U.S.A. 8:5515-5520 (2002); and Brummelkamp et al., Science 296: 550-553 (2002)).

The term "nucleic acid-based therapeutic agent" as used herein refers to three classes of compounds. The term also includes pharmaceutically acceptable salts, esters, prodrugs, codrugs, and protected forms of the compounds, analogs and derivatives described below. The first class, referred to herein collectively as "antisense nucleic acids," comprises nucleic acids, preferably oligomers of about 50 monomer units or fewer, which have the ability to hybridize in a sequence-specific manner to a targeted single-stranded RNA or DNA molecule. Members of this class include ordinary DNA and RNA oligomers, DNA and RNA having modified backbones, including but not limited to phosphorothioates, phosphorodithioates, methylphosphonates, and peptide nucleic acids, 2'-deoxy derivatives, and nucleic acid oligomers that feature chemically modified purine and pyrimidine bases, or have been lipophilically modified and/or PEGylated to modify their pharmacodynamics. Oligomers that serve as precursors for such agents, such as hairpin RNAs that are converted to siRNAs within cells, are also considered to be within this class.

The second class of nucleic acid-based therapeutic agents is aptamers. Aptamers comprises nucleic acids, preferably oligomers of about 50 monomer units or fewer, which have the ability to bind with structural specificity to a non-oligonucleotide target molecule, or to an oligonucleotide in a manner other than through sequence-specific hybridization. Members of this class include DNA and RNA aptamers, and modifications thereof including but not limited to mirror-image DNA and RNA ("Spiegelmers"), peptide nucleic acids, and nucleic acid oligomers that have otherwise been chemically modified as described above. Again, any of these species may also feature chemically modified purines and pyrimidines or may be lipophilically modified and/or PEGylated (see M. Rimmele, Chembiochem. 4: 963-71 (2003); and A. Vater and S. Klussmann, Curr. Opin. Drug Discov. Devel. 6: 253-61 (2003), for recent reviews of aptamer technology). It will be appreciated that many members of this second class will, in addition to their structure-specific affinity for the target molecule, have sequence-specific affinity for a putative DNA or RNA sequence.

The third class of nucleic acid-based therapeutic agents, referred to herein as "nucleic acid enzymes," comprises nucleic acids that are capable of recognizing and catalyzing the cleavage of target RNA molecules, in a sequence-specific manner. The class includes hammerhead ribozymes, minimized hammerheads ("minizymes"), '10-23' deoxyribozymes ("DNAzymes"), and the like. As with antisense and aptamer molecules, the class includes catalytic species that have been chemically modified.

The term "pharmaceutically acceptable salts" refers to physiologically and pharmaceutically acceptable salts of the compounds of the invention, e.g., salts that retain the desired biological activity of the parent compound and do not impart undesired toxicological effects thereto.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, the term "RNAi construct" is a generic term including siRNA, hairpin RNA, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can be converted into siRNAs in vivo.

As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an episomal vector, e.g., a nucleic acid capable of extra-chromosomal replication. Vectors capable of directing the expression of genes to which they are operatively linked are referred to herein as "expression vectors." In the present specification, "plasmid" and "vector" are used interchangeably unless otherwise clear from the context. In the expression vectors, regulatory elements controlling transcription can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

In one embodiment, the present disclosure relates to the use of antisense nucleic acid to decrease expression of a targeted disease-related protein. Such an antisense nucleic acid can be delivered, for example, as an expression plasmid which, when transcribed in the cell, produces RNA which is complementary to at least a unique portion of the cellular mRNA which encodes the targeted disease-related protein. Alternatively, the construct is an oligonucleotide which is generated ex vivo and which, when introduced into the cell causes inhibition of expression by hybridizing with the mRNA and/or genomic sequences encoding the targeted disease-related protein. Such oligonucleotides are optionally modified so as to be resistant to endogenous exonucleases and/or endonucleases. Exemplary nucleic acid molecules for use as antisense oligonucleotides are phosphoramidate, phosphothioate and methylphosphonate analogs of DNA (see for example U.S. Pat. Nos. 5,176,996; 5,264,564; and 5,256,775). General approaches to constructing oligomers useful in nucleic acid therapy have been reviewed and are well known in the art.

In other embodiments, this application relates to the use of RNA interference (RNAi) to effect knockdown of the targeted gene. RNAi constructs comprise double stranded RNA that can specifically block expression of a target gene. RNAi constructs can comprise either long stretches of dsRNA identical or substantially identical to the target nucleic acid sequence, or short stretches of dsRNA identical or substantially identical to only a region of the target nucleic acid sequence.

Optionally, the RNAi constructs may contain a nucleotide sequence that hybridizes under physiologic conditions of the cell to the nucleotide sequence of at least a portion of the mRNA transcript for the gene to be inhibited (the "target" gene). The double-stranded RNA need only be sufficiently similar to natural RNA that it has the ability to induce RNAi. Thus, the invention contemplates embodiments that are tolerant of sequence variations that might be expected due to genetic mutation, polymorphic sites, or evolutionary divergence in a targeted sequence. The number of tolerated nucleotide mismatches between the target sequence and the RNAi construct sequence may be as high as 1 in 5 base pairs, but is preferably no higher than 1 in 10 base pairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Between 90% and 100% sequence identity between the inhibitory RNA and the portion of the target gene is preferred. Alternatively, the duplex region of the RNA may be defined functionally as a nucleotide sequence that is capable of detectably hybridizing with the target gene transcript after hybridization for 12 to 16 hours at 50° C. to 70° C. in 400 mM NaCl, 40 mM PIPES pH 6.4, and 1.0 mM EDTA, followed by washing.

The double-stranded structure may be formed by a single self-complementary RNA strand or two complementary RNA strands. Formation of the dsRNA may be initiated inside or outside of the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications.

The subject RNAi constructs can be "small interfering RNAs" or "siRNAs." These nucleic acids are less than about 50, and preferably around 19-30 nucleotides in length, more preferably 21-23 nucleotides in length. The siRNAs are thought to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme DICER. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The siRNA molecules can be purified using a number of techniques known to those of skill in the art, such as gel electrophoresis. Alternatively, non-denaturing methods, such as column chromatography, size exclusion chromatography, glycerol gradient centrifugation, and affinity purification can be used to purify siRNAs.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis. Methods of chemically modifying RNA molecules can be adapted for modifying RNAi constructs (see, e.g., Heidenreich et al., Nucleic Acids Res. 25: 776-780 (1997); Wilson et al., J. Mol. Recog. 7: 89-98 (1994); Chen et al. Nucleic Acids Res., 23: 2661-2668 (1995); and Hirschbein et al., Antisense Nucleic Acid Drug, Dev. 7: 55-61 (1997)). For example, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted or 2'-deoxy ribonucleosides, α-configurations, etc.)

In some embodiments, at least one strand of the siRNA molecules may have a 3' overhang from about 1 to about 6 nucleotides in length. Preferably, the 3' overhangs are 1-3 nucleotides in length. In certain embodiments, one strand has a 3' overhang and the other strand is blunt-ended or also has an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythymidine, may be tolerated without reducing the effectiveness of the RNAi. The absence of a 2' hydroxyl significantly enhances the nuclease resistance of the overhang in tissue culture medium, and may be also beneficial in vivo.

The RNAi construct can also be in the form of a long double-stranded RNA, which is digested intracellularly to produce a siRNA sequence within the cell. Alternatively, the RNAi construct may be in the form of a hairpin RNA. It is known in the art that siRNAs can be produced by processing hairpin RNAs in the cell. Hairpin RNAs can be synthesized exogenously or can be formed by transcribing from RNA polymerase III promoters in vivo. Examples of making and using hairpin RNAs for gene silencing in mammalian cells are described in, for example, Paddison et al. (Genes Dev 16: 948-58 (2002)), McCaffrey et al. (Nature 418: 38-9 (2002)), McManus et al. (RNA 8: 842-50 (2002)), and Yu et al. (Proc. Natl. Acad. Sci. USA 99: 6047-52 (2002)). Preferably, such hairpin RNAs are engineered in cells or in an animal to ensure continuous and stable suppression of a desired gene.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In another embodiment, the present disclosure relates to the use of ribozyme molecules designed to catalytically cleave an mRNA transcript to prevent translation of the mRNA (see, e.g., PCT International Publication WO90/11364, published Oct. 4, 1990; Sarver et al., Science 247: 1222-1225 (1990); and U.S. Pat. No. 5,093,246). While any ribozyme that cleaves the target mRNA at a site-specific recognition sequence can be used to destroy that particular mRNA, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (Nature, 334: 585-591 (1988)). The ribozymes of the present invention also include RNA endoribonucleases ("Cech-type ribozymes") such as the one which occurs naturally in Tetrahymena thermophila (known as the IVS or L-19 IVS RNA) and which has been extensively described (see, e.g., Zaug, et al., Science 224: 574-578 (1984); Zaug and Cech, Science 231: 470-475 (1986); Zaug, et al., Nature 324: 429-433 (1986); published International patent application No. WO88/04300; and Been and Cech, Cell 47: 207-216 (1986)).

In a further embodiment, the invention relates to the use of DNA enzymes to inhibit expression of a targeted gene. DNA enzymes incorporate some of the mechanistic features of both antisense and ribozyme technologies. DNA enzymes are designed so that they recognize a particular target nucleic acid sequence, much like an antisense oligonucleotide; however, much like a ribozyme, they are catalytic and specifically cleave the target nucleic acid. Briefly, to design an ideal DNA enzyme that specifically recognizes and cleaves a target nucleic acid, one of skill in the art must first identify a unique (or nearly unique) target sequence. Preferably, the sequence is a G/C rich stretch of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

The methods described herein may be used to deliver a variety of molecules, including but not limited to small molecules (including small molecules that do not have optimal cell-permeability), lipids, nucleosides, nucleotides, nucleic acids, polynucleotides, oligonucleotides, antibodies, toxins, negatively charged polymers and other polymers, for example proteins, peptides, hormones, carbohydrates, or polyamines, across cellular membranes. Non-limiting examples of polynucleotides that can be delivered across cellular membranes using the compounds and methods of the invention include short interfering nucleic acid (siNA), antisense, enzymatic nucleic acid molecules, 2',5'-oligoadenylate, triplex forming oligonucleotides, aptamers, and decoys. Biologically active molecules that may be delivered include antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, allozymes, aptamers, decoys and analogs thereof, and small nucleic acid molecules, such as short interfering nucleic acid (siNA), short interfering RNA (siRNA), double-stranded RNA (dsRNA), micro-RNA (miRNA), antagomirs, and short hairpin RNA (shRNA) molecules, to relevant cells and/or tissues, such as in a subject or organism. The compounds, compositions, and methods of the invention can increase delivery or availability of biologically active molecules) to cells or tissues compared to delivery of the molecules in the absence of the compounds, compositions, and methods of the invention. As such, the level of a biologically active molecule inside a cell, tissue, or organism is increased in the presence of the compounds and compositions of the invention compared to when the compounds and compositions of the invention are absent.

In various embodiments, a biologically active molecule is a ligand. The term "ligand" refers to any compound or molecule, such as a drug, peptide, hormone, or neurotransmitter that is capable of interacting with another compound, such as a receptor, either directly or indirectly. The receptor that interacts with a ligand can be present on the surface of a cell or can alternately be an intercellular receptor. Interaction of the ligand with the receptor can result in a biochemical reaction, or can simply be a physical interaction or association. Non-limiting examples of ligands include sugars and carbohydrates such as galactose, galactosamine, and N-acetyl galactosamine; hormones such as estrogen, testosterone, progesterone, glucocortisone, adrenaline, insulin, glucagon, cortisol, vitamin D, thyroid hormone, retinoic acid, and growth hormones; growth factors such as VEGF, EGF, NGF, and PDGF; cholesterol; bile acids; neurotransmitters such as GABA, Glutamate, acetylcholine; NOGO; inositol triphosphate; diacylglycerol; epinephrine; norepinephrine; Nitric Oxide, peptides, vitamins such as folate and pyridoxine, drugs, antibodies and any other molecule that can interact with a receptor in vivo or in vitro. The ligand can be attached to a conjugate of the invention using a linker molecule, such as an amide, amido, carbonyl, ester, peptide, disulphide, silane, nucleoside, abasic nucleoside, polyether, polyamine, polyamide, peptide, carbohydrate, lipid, polyhydrocarbon, phosphate ester, phosphoramidate, thiophosphate, alkylphosphate, or photolabile linker. In one embodiment, the linker is a biodegradable linker.

A variety of linkers may be used to link portions of the conjugates described herein. The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage. The term "photolabile linker" as used herein, refers to linker moieties as are known in the art that are selectively cleaved under particular UV wavelengths. Compounds of the invention containing photolabile linkers can be used to deliver compounds to a target cell or tissue of interest, and can be subsequently released in the presence of a UV source.

The term "linker" as used herein is any bond, small molecule, or other vehicle which allows the substrate and the active agent to be targeted to the same area, tissue, or cell, for example by physically linking the individual portions of the conjugate.

In certain embodiments, a cleavable or degradable linker may be used. In one embodiment the linker is a chemical bond between one or more substrates and one or more therapeutic moieties. Thus, the bond may be covalent or ionic. An example of a therapeutic complex where the linker is a chemical bond would be a fusion protein. In one embodiment, the chemical bond is acid sensitive and the pH sensitive bond is cleaved upon going from the blood stream (pH 7.5) to the transcytotic vesicle or the interior of the cell (pH about 6.0). Alternatively, the bond may not be acid sensitive, but may be cleavable by a specific enzyme or chemical which is subsequently added or naturally found in the microenvironment of the targeted site. Alternatively, the bond may be a bond that is cleaved under reducing conditions, for example a disulfide bond.

Alternatively, the bond may not be cleavable. Any kind of acid cleavable or acid sensitive linker may be used. Examples of acid cleavable bonds include, but are not limited to: a class of organic acids known as cipolycarboxylic alkenes. This class of molecule contains at least three carboxylic acid groups (COOH) attached to a carbon chain that contains at least one double bond. These molecules as well as how they are made and used is disclosed in Shen, et al. U.S. Pat. No. 4,631,190.

Alternatively, molecules such as amino-sulfhydryl cross-linking reagents which are cleavable under mildly acidic conditions may be used. These molecules are disclosed in U.S. Pat. No. 4,569,789.

Alternatively, the acid cleavable linker may be a time-release bond, such as a biodegradable, hydrolyzable bond. Typical biodegradable carrier bonds include esters, amides or urethane bonds, so that typical carriers are polyesters, polyamides, polyurethanes and other condensation polymers having a molecular weight between about 5,000 and 1,000,000.

Examples of these carriers/bonds are shown in U.S. Pat. No. 4,356,166. Other acid cleavable linkers may be found in U.S. Pat. Nos. 4,569,789 and 4,631,190 or Blattner et al. (Biochemistry 24:1517-1524 (1984)). The linkers are cleaved by natural acidic conditions, or alternatively, acid conditions can be induced at a target site as explained in U.S. Pat. No. 4,171,563.

Examples of linking reagents which contain cleavable disulfide bonds (reducable bonds) include, but are not limited to "DPDPB", 1,4-di-[3'-(2'-pyridyldithio) propionamido]butane; "SADP", (N-succinimidyl (4-azidophenyl) 1,3'-dithiopropionate); "Sulfo-SADP" (Sulfosuccinimidyl (4-azidophenyldithio) propionate; "DSP"-Dithio bis (succinimidylproprionate); "DTSSP"-3,3'-Dithio bis (sulfosuccinimidylpropionate); "DTBP"-dimethyl 3,3dithiobispropionimidate-2HCI.

Examples of linking reagents cleavable by oxidation are "DST"-disuccinimidyl tartarate; and "Sulfo-DST"-disuccinimidyl tartarate.

Examples of non-cleavable linkers are "Sulfo-LC-SMPT"-(sulfosuccinimidyl 6-[alphamethyl-alpha-(2-pyridylthio) toluamido}hexanoate; "SMPT"; "ABH"-Azidobenzoyl hydrazide; "NHS-ASA"-N-Hydroxysuccinimidyl-4-azidosalicyclic acid; "SASD"-Sulfosuccinimidyl 2-(pazidosalicylamido)ethyl-1,3-dithiopropionate; "APDP"-N-{4-(p-azidosalicylamido) buthy}-3' (2'-pyidyldithio)propionamide; "BASED"-Bis-[β-(4-azidosalicylamido)ethyl]disulfide; "HSAB"-N-hydroxysuccinimidyl-4 azidobenzoate; "APG"-p-Azidophenyl glyoxal monohydrate; "SANPAH"-N-Succiminidyl-6 (4'-azido-2'-mitrophenyl-amino) hexanoate; "Sulfo-SANPAH"-Sulfosuccinimidyl6-(4'-azido-2'-nitro-phenylamino) hexanoate; "ANB-NOS" N-5-Azido-2-nitrobenzyoyloxysuccinimide; "SAND"-Sulfosuccinimidyl-2-(m-azido-o-mitrobenzamido)-ethyl-1,3'-dithiopr-opionate; "PNP-DTP"-p-nitrophenyl-2-diazo-3,3,3-trifluoropropionate; "SMCC"-Succinimidyl-4-(N-maleimidomethyl)cyclohexane-1-carboxylate; "Sulfo-SMCC"-Sulfosuccinimidyl-4-(N-maleimidomethyl)cyclohexane-1-carboxy-late; "MBS" m-Maleimidobenzoyl-N-hydroxysuccinimide ester; "sulfo-MBS"-m-Maleimidobenzoyl-N-hydroxysulfosuccinimide ester; "SIAB"-N-Succinimidyl (4-iodoacetyl)aminobenzoate; "SulfSIAB"-N-Sulfosuccinimidyl (4-iodoacetyl)aminobenzoate; "SMPB"-Succinimidyl 4-(pmalenimidophenyl) butyrate; "Sulfo-SMPB"-Sulfosuccinimidyl 4-(p-malenimidophenyl) butyrate; "DSS"-Disuccinimidyl suberate; "BSSS"-bis(sulfosuccinimidyl) suberate; "BMH"-Bis maleimidohexane; "DFDNB"-1,5-difluoro-2,4-dinitrobenzene; "DMA"-dimethyl adipimidate 2HCI; "DMP"-Dimethyl pimelimidate-2HCI; "DMS"-dimethyl suberimidate-2-HCl; "SPDPN-succinimidyl-3-(2-pyridylthio) propionate; "Sulfo-HSAB"-Sulfosuccinimidyl 4-(pazidophenyl) butyrate; "Sulfo-SAPB"-Sulfosuccinimidyl 4-(p-azidophenylbutyrate); "ASIB"-1-9p-azidosalicylamido)-4-(iodoacetamido) butane; "ASBA"-4-(p-Azidosalicylamido) butylamine.

In another embodiment the linker is a small molecule such as a peptide linker. In one embodiment the peptide linker is not cleavable. In a further embodiment the peptide linker is cleavable by base, under reducing conditions, or by a specific enzyme. In one embodiment, the enzyme is indigenous. Alternatively, the small peptide may be cleavable by an non-indigenous enzyme which is administered after or in addition to the therapeutic complex. Alternatively, the small peptide may be cleaved under reducing conditions, for example, when the peptide contains a disulfide bond. Alternatively, the small peptide may be pH sensitive.

The peptide linker may also be useful as a peptide tag (e.g., myc or $His_6$ (SEQ ID NO: 9)) or may be one or more repeats of the known linker sequence GGGGS (SEQ ID NO: 10). The skilled artisan will recognize that the linker sequence may be varied depending on the polypeptide portions to be linked to form the conjugate. Additional peptide linkers and tags are known in the art, such as epitope tags, affinity tags, solubility enhancing tags, and the like. Examples of various additional tags and linkers that may be used with the present invention include, hemagglutinin (HA) epitope, myc epitope, chitin binding protein (CBP), maltose binding protein (MBP), glutathione-S-transferase (GST), calmodulin binding peptide, biotin carboxyl carrier protein (BCCP), FLAG octapeptide, nus, green fluorescent protein (GFP), thioredoxin (TRX), poly(NANP), V5, S-protein, streptavidin, SBP, poly(Arg), DsbA, c-myc-tag, HAT, cellulose binding domain, softag 1, softag3, small ubiquitin-like modifier (SUMO), and ubiquitin (Ub). Further examples include: poly(L-Gly), (Poly L-Glycine linkers); poly(L-Glu), (PolyL-Glutamine linkers); poly (L-Lys), (Poly L-Lysine linkers). In one embodiment, the peptide linker has the formula (amino acid) n, where n is an integer between 2 and 100, preferably wherein the peptide comprises a polymer of one or more amino acids.

In a further embodiment, the peptide linker is cleavable by proteinase such as one having the amino acid sequence GFPRGFPAGG (SEQ ID NO: 11). This embodiment has been shown to be advantageous for the treatment of bacterial infections, particularly *Pseudomonas aeruginosa*. Gentamicin or an alternate antibiotic is cleaved only when the wounds are infected by *Pseudomonas aeruginosa* because there is significantly higher activity of thrombin-like proteinase enzymes then in noninfected tissue.

In a further embodiment the linker is a cleavable linker including, poly (ethylene glycol) (PEG) and a dipeptide,L-alanyl-L-valine (Ala-Val), cleavable by the enzyme thermolysin. This linker is advantageous because thermolysin-like enzyme has been reported to be expressed at the site of many tumors. Alternatively, a 12 residue spacer TRHRQPRG-WEQL (SEQ ID NO: 12) may be used which contains the recognition site for the protease furin.

The chemical and peptide linkers can be bonded between the substrate and the active agent by techniques known in the art for conjugate synthesis, i.e. using genetic engineering, or chemically. The conjugate synthesis can be accomplished chemically via the appropriate antibody by classical coupling reactions of proteins to other moieties at appropriate functional groups.

Examples of the functional groups present in proteins and utilized normally for chemical coupling reactions are outlined as follows. The carbohydrate structures may be oxidized to aldehyde groups that in turn are reacted with a compound containing the groupH2NNH—R (wherein R is the compound) to the formation of a C=NH—NH—R group. The thiol group (cysteines in proteins) may be reacted with a compound containing a thiol-reactive group to the formation of a thioether group or disulfide group. The free amino group (at the amino terminus of a protein or on a lysine) in amino acid residues may be reacted with a compound containing an electrophilic group, such as an activated carboxy group, to the formation of an amide group. Free carboxy groups in amino acid residues may be transformed to a reactive carboxy group and then reacted with a compound containing an amino group to the formation of an amide group.

The linker may alternatively be a liposome. Many methods for the preparation of liposomes are well known in the art. For example, the reverse phase evaporation method, freezethaw methods, extrusion methods, and dehydration-rehydration methods (see, Storm et al., PSTT 1:19-31 (1998)).

The liposomes may be produced in a solution containing the active agent so that the substance is encapsulated during polymerization. Alternatively, the liposomes can be polymerized first, and the biologically active substance can be added later by resuspending the polymerized liposomes in a solution of a biologically active substance and treating with sonication to affect encapsulation of the active agent. The liposomes can be polymerized in the presence of the substrate such that the substrate becomes a part of the phospholipid bilayer. In one embodiment, the liposome contains the active agent on the inside and the substrate on the outside.

The liposomes contemplated in the present invention can comprise a variety of structures. For example, the liposomes can be multilamellar large vesicles (MLV), oligolamellar vesicles (OLV), unilamellar vesicles (UV), small unilamellar vesicles (SUV), medium sized unilamellar vesicles (MUV), large unilamellar vesicles (LUV), giant unilamellar vesicles (GUY), or multivesicular vesicles (MVV). Each of these liposome structures are well known in the art (see, Storm et al., PSTT 1:19-31 (1998)).

In one embodiment, the liposome is a "micromachine" that evulses pharmaceuticals for example by the application of specific frequency radio waves. In another embodiment, the liposomes can be degraded such that they will release the active agent in the targeted cell, for example, the liposomes may be acid or alkaline. sensitive, or degraded in the presence of a low or high pH, such that the active agent is released within the cell. Alternatively, the liposomes may be uncharged so that they will be taken up by the targeted cell. The liposomes may also be pH sensitive or sensitive to reducing conditions.

One type of liposome which may be advantageously used in the present invention is that identified in U.S. Pat. No. 6,004,534. In this application a method of producing modified liposomes which are prepared by polymerization of double and triple bond-containing monomeric phospholipids is disclosed. These liposomes have surprisingly enhanced stability against the harsh environment of the gastrointestinal tract. Thus, they have utility for oral and/or mucosal delivery of the active agent. It has also been shown that the liposomes may be absorbed into the systemic circulation and lymphatic circulation. The liposomes are generally prepared by polymerization (i.e., radical initiation or radiation) of double and triple bond-containing monomeric phospholipids.

In other embodiments of the present invention, the linker can also be a liposome having a long blood circulation time. Such liposomes are well known in the art (see U.S. Pat. Nos. 5,013,556; 5,225,212; 5,213,804; 5,356,633; and 5,843,473). Liposomes having long blood circulation time are characterized by having a portion of their phospholipids derivatized with polyethylene glycol (PEG) or other similar polymer. In some embodiments, the end of the PEG molecule distal to the phospholipid may be activated so a to be chemically reactive. Such a reactive PEG molecule can be used to link a substrate to the liposome. One example of a reactive PEG molecule is the maleimide derivative of PEG described in U.S. Pat. No. 5,527,528).

Alternatively, the linker may be a microcapsule, a nanoparticle, a magnetic particle, and the like (see Kumar, J. Pharm. Sci. 2:234-258 (2000); and Gill et al., Trends Biotechnol. 18(11):469-79 (2000)), with the lipophilic active agent on or in the container, and the container functioning as the linker in the therapeutic complex.

Alternatively, the linker may be a photocleavable linker. For example, a 1-2-(nitrophenyl)ethyl moiety can be cleaved using 300 to 360 nm light. It can be envisioned that the photocleavable linker would allow activation and action of the drug in an even more specific area, for example a particular part of the organ. The light could be localized using a catheter into the vessel. Alternatively, light may be used to localize treatment to a specific part of the digestive tract and the light may be manipulated through a natural orifice to the area. Alternatively, the light can be surgically manipulated to the area.

Alternatively, the linker may not be cleavable, but the active agent or substrate is. An example of this is when the active agent is a prodrug and the enzyme which cleaves the prodrug is administered with the therapeutic complex. Alternatively, the enzyme is part of the therapeutic complex or indigenous and the prodrug is administered separately. Preferably, the enzyme or prodrug which is administered separately is administered within about 48 hours of the first administration. Alternatively, the prodrug or enzyme which is administered separately may be administered between about 1 min and 24 hours, alternatively between about 2 min and 8 hours. The prodrug or enzyme which is administered separately, may be readministered at a later date and may continue to be administered until the effect of the drug is not longer needed.

According to yet another embodiment of the invention, there are provided methods for treating a disease or disorder in a cell or tissue expressing a nucleoside transport pathway. The method includes administering to a patient having the disease or disorder a conjugate including a substrate that is capable of being transported by the nucleoside transport pathway expressed in the affected cell or tissue and an active agent for treating disease or disorder, wherein the conjugate is also transported by the nucleoside transport pathway. In this way, the conjugate is transported into the affected cells or tissue, thereby delivering the active agent.

Diseases or disorders which may be treated using a conjugate of the invention include diseases or disorders involving tissues such as muscle (including skeletal muscle and cardiac muscle), glycogen-storing cells, vascular endothelium, heart, brain, placenta, thymus, pancreas, prostate, kidney, blood, skin, and ENT2-expressing cancer cells.

In certain embodiments the disease or disorder involves muscle such as skeletal or cardiac muscle and the conjugate is transported into the muscle cells (such as skeletal muscle cells or cardiac muscle cells), thereby delivering the active agent. In certain embodiments, the muscle disorder is selected from the group consisting of cachexia, muscle dystrophies, lysosomal muscle disorders, skeletal muscle disorders, smooth muscle disorders, and cardiac muscle disorders. In certain embodiments, these designations may overlap. Muscle dystrophies include Becker's muscular dystrophy (BMD), Congenital muscular dystrophy, Duchenne muscular dystrophy (DMD), Distal muscular dystrophy, Emery-Dreifuss muscular dystrophy, Facioscapulohumeral muscular dystrophy (FSHD), Limb-girdle muscular dystrophy (LGMD), Myotonic muscular dystrophy, and Oculopharyngeal muscular dystrophy. In certain embodiments, a lysosomal disorder is Pompe Disease, Hurler Syndrome, Fabry Disease, Maroteaux-Lamy Syndrome, Morquio Syndrome, Hunter Syndrome, Farber Disease, Krabbe Disease, Sly Syndrome, Sanfilippo (including A, B, and D), Morquio A, Multiple Sulfatase Deficiency, Metachromatic Leukodystrophy, Mucolipidosis IV, G.sub.MI Gangliosidosis, Galactosialidosis, Tay-Sachs and Tay-Sachs Variants, Sandhoff, Fucsidosis, Schindler Disease, Sialidosis, Aspartylglucosaminuria, Wolman Disease, Farber Lipogranulomatosis, and Nieman-Pick disease. In certain embodiments, the cardiac muscle disorder is cardiomyopathy, cardiac ischemia, congestive heart failure, ischemia-reperfusion injury, Coronary heart disease, Cardiovascular disease, Ischaemic heart disease, Heart failure, Hypertensive heart disease, Inflammatory heart disease, and Valvular heart disease. The muscle disorder may be sarcopenia. In some embodiments, the muscle disorder is muscle wasting caused by another disease, such as AIDS or cancer. Other muscle disorders include diseases of the neuromuscular junction, such as myasthenia gravis, Lambert-Eaton syndrome, and Congenital Myasthenic Syndrome, motor neuron diseases (such as ALS, spinal muscular atrophy, Charcot-Maria-Tooth disease, and Freidrich's Ataxia), inflammatory myopathies (such as dermatomyositis, polymyositis, and inclusion body myositis), endocrine abnormalities (such as hyperthyroid myopathy), myotonia, nemaline myopathy, and myotubular myopathy. Enzyme deficiency disorders of the muscles include Phosphorylase Deficiency, Acid Maltase Deficiency, Mitochondrial Myopathy, Carnitine Palmityl Transferase Deficiency, Phosphoglycerate Kinase Deficiency, and Phosphoglycerate Mutase Deficiency.

In particular embodiments, the active agent effective in the treatment of a skeletal muscle disorder may be, for example, an enzyme that is lacking in a patient with the muscle disorder. For example, the following skeletal muscle diseases and disorders may be treated with the following enzymes, or a nucleic acid that modulates the expression of said enzymes, in accordance with the methods herein: α-glucosidase (Pompe Disease), α-L-iduronidase (Hurler Syndrome), α-galactosidase A (Fabry Disease), arylsulfatase (Maroteaux-Lamy Syndrome), N-acetylgalactosamine-6-sulfatase or β-galactosidase (Morquio Syndrome), iduronate 2-sulfatase (Hunter Syndrome), ceramidase (Farber Disease), galactocerebrosidase (Krabbe Disease), β-glucuronidase (Sly Syndrome), Heparan N-sulfatase (Sanfilippo A), N-Acetyl-α-glucosaminidase (Sanfilippo B), Acetyl CoA-α-glucosaminide N-acetyl transferase, N-acetyl-glucosamine-6 sulfatase (Sanfilippo D), Galactose 6-sulfatase (Morquio A), Arylsulfatase A, B, and C (Multiple Sulfatase Deficiency), Arylsulfatase A Cerebroside (Metachromatic Leukodystrophy), Ganglioside (Mucolipidosis IV), Acid β-galactosidase $G_{MI}$ Gaiglioside ($G_{MI}$ Gangliosidosis), Acid β-galactosidase (Galactosialidosis), Hexosaminidase A (Tay-Sachs and Variants), Hexosaminidase B (Sandhoff), α-fucosidase (Fucsidosis), α-N-Acetyl galactosaminidase (Schindler Disease), Glycoprotein Neuraminidase (Sialidosis), Aspartylglucosamine amidase (Aspartylglucosaminuria), Acid Lipase (Wolman Disease), Acid Ceramidase (Farber Lipogranulomatosis), Lysosomal Sphingomyelinase and other Sphingomyelinase (Nieman-Pick). In certain embodiments, the active agent is dystrophin, components of dystrophin-glycoprotein complex, the laminin-α2 chain, fukutin-related protein, LARGE, fukutin, EMD, LMNA, DMPK, ZNF9, and PABPN1, or a nucleic acid that modulates the expression of said proteins.

In certain embodiments the disease or disorder involves glycogen-storing cells and the conjugate is transported into the glycogen-storing cells, thereby delivering the active agent. Glycogen-storing cells include muscle cells, liver cells, and also kidney and intestinal cells. In certain embodiments, the glycogen-storage disorder is selected from the group consisting of Glycogen synthase deficiency, Glucose-6-phosphatase deficiency (von Gierke disease), Debranching enzyme deficiency (Forbes-Cori disease), Transglucosidase deficiency, (Andersen disease, amylopectinosis), Myophosphorylase deficiency (McArdle disease), Phosphorylase deficiency (Hers disease), and Phosphofructokinase deficiency (Tauri disease). In particular embodiments, the active agent effective in the treatment of a glycogen-storage disorder is Glycogen synthase, Glucose-6-phosphatase, Debranching enzyme, Transglucosidase, Myophosphorylase, Phosphorylase, Phosphofructokinase, Acid Maltase Deficiency, Carnitine Palmityl Transferase, Phosphoglycerate Kinase, or Phosphoglycerate Mutase, or a nucleic acid that up-regulates the expression of the deficient proteins.

In certain embodiments the disease or disorder involves vascular endothelium and the conjugate is transported into the vascular endothelium, thereby delivering the active agent. In certain embodiments, the vascular endothelium disorder is selected from the group consisting of inappropriate angiogenesis (for example, surrounding a tumor), deficient angiogenesis (for example, in a slowly-healing wound or ulcer), restenosis, atherosclerosis, scarring after surgery or injury, and vasculitis. Examples of diseases associated with uncontrolled angiogenesis that may be treated with the compositions and methods herein include, but are not limited to retinal/choroidal neovascularization and corneal neovascularization. Examples of retinal/choroidal neovascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma. Example of deficient angiogenesis include ulcers such as skin ulcers and diabetic ulcers. In one embodiment, the active agent effective in the treatment of a disease of the vascular endothelium is serum amyloid P (SAP), or a nucleic acid that increases SAP expression. SAP inhibits fibrocytes from causing pathological scarring lesions. In another embodiment, the disease of the vascular endothelium is atherosclerosis, which may be treated using statins, niacin, intestinal cholesterol absorption-inhibiting supplements such as ezetimibe and fibrates, aspirin, human Apo-A1 Milano HDL, or a nucleic acid that increases Apo-A1 Milano HDL expression. One may also administer nucleic acids that reduce synthesis of cholesterol, such as siRNA constructs designed to reduce expression of cholesterol synthetic enzymes. Cholesterol synthetic enzymes include HMG-CoA synthase, HMG-CoA reductase, mevalonate kinase, phosphomevalonate kinase, and lanosterol synthase.

In certain embodiments the disease or disorder involves the brain and the conjugate is transported into the brain cells, thereby delivering the active agent. In certain embodiments, the brain disorder is selected from the group consisting of neurodegenerative diseases (such as Alzheimer's disease, Parkinson's disease, motor neuron disease, and Huntington's disease), mental illnesses, such as clinical depression, schizophrenia, bipolar disorder, and post-traumatic stress disorder; infectious diseases including meningitis, viral, bacterial, and prion diseases, inherited disorders such as Tay-Sachs disease, Fragile X syndrome, and Down syndrome, and lysosomal storage disorders. In particular embodiments, the active agent effective in the treatment of a disease of the brain is an enzyme absent (or present at reduced levels) in a patient with a lysosomal storage disorder; examples of lysosomal disorders, and compositions for treating them, are listed above.

In certain embodiments the disease or disorder involves the placenta and the conjugate is transported into the placental cells, thereby delivering the active agent. In certain embodiments, the placental disorder is selected from the group consisting of Placenta accreta, Placenta praevia, and Placental abruption.

In certain embodiments the disease or disorder involves the thymus and the conjugate is transported into cells of the thymus, thereby delivering the active agent. In certain embodiments, the thymus disorder is selected from the group consisting of an autoimmune disease, a disease resulting from faulty positive selection or faulty negative selection of T cells, and cancer of the thymus. Some examples of autoimmune diseases include Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyclinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barr, Hashimoto's Thyroiditis, Hypothyroidism, Idiopathic Pulmonary Fibrosis, Idiopathic Thrombocytopenia Purpura (ITP), IgA Nephropathy, Insulin dependent Diabetes, Juvenile Arthritis, Lichen Planus, Lupus, Meniere's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, and myasthenia gravis. In particular embodiments, the active agent effective in the treatment of a disease of the thymus is immunosuppressive or anti-inflammatory. The agent may be, for example, an antibody including muromab, basiliximab, and daclizumab, or a nucleic acid encoding one of those antibodies. Examples of immunosuppressive and anti-inflammatory drugs that may be used as the active agent include corticosteroids, rolipram, calphostin, CSAIDs; interleukin-10, glucocorticoids, salicylates, nitric oxide; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-α inhibitors such as tenidap, anti-TNF antibodies or soluble TNF receptor, and rapamycin (sirolimus or Rapamune) or derivatives thereof. When the disease is cancer of the thymus, the active agent may be a chemotherapeutic drug or other type of anti-cancer therapeutic.

In certain embodiments the disease or disorder involves the pancreas and the conjugate is transported into cells of the pancreas, thereby delivering the active agent. In certain embodiments, the pancreas disorder is selected from the group consisting of Pancreatitis, Diabetes mellitus, Exocrine pancreatic insufficiency, complications of Cystic fibrosis, Pseudocysts, or pancreatic cancer. In particular embodiments, the active agent effective in the treatment of a disease of the pancreas is insulin, a Pancreatic Enzyme Product (PEP) such as pancrelipase, or a nucleic acid that up-regulates expression of the same.

In certain embodiments the disease or disorder involves the prostate and the conjugate is transported into cells of the prostate, thereby delivering the active agent. In certain embodiments, the prostate disorder is selected from the group consisting of Prostatitis, Benign prostatic hyperplasia, or Prostate cancer. In particular embodiments, the active agent effective in the treatment of a disease of the prostate is an anti-cancer agent; examples of such agents are listed elsewhere in this application.

In certain embodiments the disease or disorder involves the kidney and the conjugate is transported into cells of the kidney, thereby delivering the active agent. In certain embodiments, the kidney disorder is selected from the group consisting of Diabetic nephropathy, Glomerulonephritis, Hydronephrosis, Kidney stones, Kidney tumors (such as Wilms tumor and Renal cell carcinoma), Lupus nephritis, Minimal change disease, Pyelonephritis, nephrotic syndrome, and Renal failure (such as Acute renal failure and Stage 5 Chronic Kidney Disease). In particular embodiments, the active agent effective in the treatment of a disease of the kidney is an agent that treats autoimmune disease, or an anti-cancer therapeutic, both of which are listed elsewhere in the present application.

In certain embodiments the disease or disorder involves the blood and the conjugate is transported into cells of the blood, thereby delivering the active agent. In certain embodiments, the blood disorder is selected from the group consisting of: primary immunodeficiency (including SCID, hemophilia A, and hemophilia B), reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leukopenia, thrombocytopenia, anemia, bone marrow disorders caused by radiation, chemical or chemotherapeutic induced bone marrow aplasia or myelosuppression, acquired immune deficiency syndrome, and polycythemia rubra vera. In particular embodiments, the active agent effective in the treatment of a disease of the blood is selected from the group consisting of corticosteroids, anti-leukemic agents, growth factors, and clotting factors. In certain embodiments, the clotting factor is Factor VIII or IX. In certain aspects, SCID is caused by a recessive mutation and may be treated by administering a wild-type copy of the missing protein (or a nucleic acid encoding that protein). For example, X-linked SCID may be treated with IL2RG, Jak3 gene mutations may be treated with JAK3, ADA gene mutations may be treated with ADA, IL-7R α-chain mutations may be treated with IL7R α, CD3 δ or ε mutations may be treated with CD3 delta or epsilon, RAG1/RAG2 mutations may be treated with RAG1/RAG2, Artemis gene mutations may be treated with ARTEMIS, and CD45 gene mutations may be treated with CD45. Other types of primary immunodeficiency are deficiencies in the following proteins: DNA ligase type I, CD40 ligand, CD40, Purine nucleoside phosphorylase (PNP), MHC class II, CD3γ, CD8, ZAP-70, TAP-1/2, Winged helix protein, CD19, TACI, BAFF receptor, AICDA, uracil-DNA glycosylase, perforin, MUNC13D, syntaxin 11, CD95, Fas ligand, CASP8, and CASP10. These deficiencies may be treated by administration of the deficient protein or a nucleic acid encoding it.

In certain embodiments the disease or disorder involves the skin and the conjugate is transported into cells of the skin, thereby delivering the active agent. In certain embodiments, the skin disorder is selected from the group consisting of dermatomyositis, papulosquamous dermatoses, bacterial dermatoses, viral dermatoses, mycolic skin infections, granulomatous dermatoses, parasitic skin dermatoses, exfoliative dermatitis, bullous dermatoses, pigmented dermatoses, photosensitive dermatoses, dermatoses caused by collagen diseases, dermatoses due to internal diseases, xerosis, urticaria, atopic dermatitis, eczyrna, lichen simplex chronicus, psoriasis, scabies, wound, sun burn, cold sores, acne, insect bite, radiotherapy or chemotherapy-induced dermatitis, paraneoplastic syndrome, malignancy, melanoma, primary skin cancer, and metastatic skin cancer. In particular embodiments, the active agent effective in the treatment of a disease of the skin is anthralin, calpotriene, coal tar, diclofenac, T4 endonuclease, isotretinoin, acitretin, cidofoir, a corticosteroid, an antibiotic, an analgesic, an immunomodulator, including oral immunomodulator such as tacrolimus and pimecrolimus, and topical immunomodulators; an immunosuppressant, an anti-angiogenic, including anti-VEGF, anti-FGF, anti-EGF and anti-HGF; a leukotriene modifier, an aminosalicylate, an anesthetic, a non-steroidal anti-inflammatory, a modifier of a solubilized interleukin receptor, an inhibitor of a tyrosine-kinase receptor, a protein kinase C inhibitor, methotrexate, cyclosporine, and methylprednisolone acetate.

In certain embodiments the disease or disorder is a type of cancer and the conjugate is transported into cancer cells, thereby delivering the active agent. In certain embodiments, the type of cancer is selected from the group consisting of rhabdomyosarcoma, ovarian cancer, colon cancer, and breast cancer. In other embodiments, the cancer is selected from leukemia, lymphomas, melanomas, squamous cell carcinomas, breast cancer, prostate cancer, bladder cancer, lung cancer including non small-cell lung cancer and small-cell lung cancer, ovarian cancer, colon cancer, squamous cell carcinoma, astrocytoma, Kaposi's sarcoma, glioblastoma, bladder cancer, head and neck cancer, glioma, colorectal cancer, genitourinary cancer and gastrointestinal cancer. In certain embodiments, the active agent is a chemotherapeutic drug. Chemotherapeutic drugs are well-known in the art and include alkylating agents such as cisplatin, anti-metabolites such as mercaptopurine, taxanes such as paclitaxel, topoisomerase inhibitors such as topotecan, and antitumor antibiotics such as doxorubicin. Anti-tumor active agents also include antibodies such as Herceptin™. In particular embodiments, the active agent effective in the treatment of cancer is a protein (or nucleic acid encoding the same) selected from: a bispecific antibody that binds Pax-FKHR fusion protein or a tumor suppressor such as p53, pRb, PTEN, APC, and CD95, BRCA1, BRCA2, DNA repair enzymes, proapoptotic genes, p16.sup.INK4a, WT1, NF1 (neurofibromin 1), NF2 (merlin or neurofibromin 2), TSC1 (hamartin), TSC2 (tuberin), DPC4, SMAD4, DCC, LKB1, STK11, MSH2, MLH1, CDH1 (E-cadherin), VHL, PTCH, (patched), MENI, BLM, NBS1, MRE11A, ATM, hRad50, NER enzymes (such as XPA, XPB, XPC, XPD, DDB2, ERCC4, RAD2, and POLH), ERCC6, ERCC8, RECQL2, FANCA, FANCC, FANCD2, FANCE, FANCF, FANCG, FANCI, FANCJ, FANCL, FANCM, MLH1, MSH2, MSH6, PMS, and PMS2.

In certain embodiments the compositions and methods herein may be used to treat a disease or disorder involving dysfunction of nuclear receptors, and the conjugate is transported into cells in which altered nuclear receptor function is desired. In certain embodiments, the nuclear receptors are steroid, thyroid, retinoid, or orphan nuclear receptors. In certain embodiments, the orphan nuclear receptor is a SAR (selective androgen receptor), PPAR, PPARβ, PPAR, NUC1, FAAR, PPAR, RevErbA, EAR-1, RVR, RevErbAβ, BD73, HZF2, ROR, RZR, RORβ, RZR13, ROR, TOR, LXR, RLD1, LXRβ, UR, NER, RIP15, OR1, FXR, RIP14, HRR1, PXR.1, PXR.2, SXR, ONR1, xOR6, BXR, hCAR1, MB67, mCAR1, HNF4, HNF4β, HNF4, RXR, RXRβ, H2RIIBP, RXR, TR2, TR2-11, xDOR2, aDOR1, TR4, TAK1, TR2R1, Tlx, TLL, xTLL, COUP-TFI, COUPTFA, EARS, SVP44, COUP-TFII, COUPTFB ARPI, SVP40, xCOUP-TFIII, COUP-TF, SVP46, EAR2, ERR, ERR1, ERRβ, ERR2, ERR, NGFI-B, NUR77, N10, TR3, NAKI, TISI, NURR1, NOT, RNR1, HZF-3, TINUR, TR3β, NOR-1, MINOR, TEC, CHN, FTZ-F1, SF1, ELP, AD4BP, FTF, LRH1, PHR1, CPF, FFLR, FF1rA, GCNF, RTR, DAX1, AHCH, or SHP. Depending on the disease to be treated, one of skill in the art will recognize whether the disease should be treated by increasing the levels of a nuclear receptor or decreasing the levels or activity of a nuclear receptor. Levels of the nuclear receptor may be increased, for example, by administering a nucleic acid encoding the nuclear receptor. Activity of the nuclear receptor may be decreased, by example, by administering an inhibitory antibody. Nuclear receptors, and the diseases caused by mutations in them, are as follows: Androgen receptor (CAIS/PAIS, complete/partial androgen insensitivity syndrome; Gynecomastia; interfility; SBMA; Kennedy's disease; Prostate Cancer; perineal hypospadias), DAX-1 (adrenal hypoplasia congenita, Adrenal insufficiency, delayed-onset, and hypogonadotropic hypogonadism), Vitamin 3D receptor (Vitamin D Resistant-rickets type IIA); HNF4 α (Maturity-onset diabetes of the young); Mineralocoricoid receptor (Pseudohypoaldosteronism, type 1; autosomal dominant; Hypertension, early-onset, autosomal dominant, with exacerbation in pregnancy), Thyroid hormone β-1 (thyroid hormone resistance), Glucocorticoid receptor (Primary cortisol resistance familial Glucocorticoid resistance), PPAR γ (Diabetes Mellitus, insulin-resistant, with acanthosis nigricans and hypertension; colon cancer; Inflammatory bowel disease), HNF4 α (Type II Diabetes), and ERa (Osteoporosis, Breast cancer). In particular embodiments, the active agent effective in the treatment of a nuclear receptor-mediated disorder is the protein deficient in the above-mentioned diseases, or a nucleic acid that up-regulates its expression. Those of the above diseases that are caused by inappropriately high expression of the mutant gene may be treated by administering a nucleic acid that down-regulates its expression.

In some aspects, a skeletal muscle disorder may be treated by altering the activity and/or levels of an orphan nuclear receptor. Orphan nuclear receptors and diseases associated with them are known in the art, for example in Smith et al., "Orphan Nuclear Receptors: therapeutic opportunities in skeletal muscle" Am J Physiol Cell Physiol 291:203-217, 2006. For example, dysfunction of LXR-α, LXR-β, farnesoid X receptor (FXR), PPAR-α, -β/δ, and -γ, liver receptor homolog-1, and the small heterodimeric partner can cause dyslipidemia, diabetes, obesity, inflammation, and cardiovascular disease. In addition, ERR-α, ROR-α, Rev-erb-α and -β, and Nur77 control several processes including lipid absorption, lipolysis, inflammation, and myokine expression. Specifically, PPAR-δ coordinates glucose tolerance, fatty acid oxidation, and energy expenditure in skeletal muscle as well as in adipose tissue. PPAR-A regulates fatty acid oxidation, and stimulates mitochondrial β-oxidation and thermogenesis in the muscles. In addition, LXR-α and -β regulate lipid metabolism in skeletal muscle. ERR-α, -β, and -γ are involved in ovesity, lipid metabolism, and oxidative phosphorylation, and mitochondrial respiration in skeletal and cardiac muscle. Also, ROR nuclear receptors (including ROR-α1, -α2, α3, and -αα) are involved in muscle dysfunction such as ataxia, as well as dyslipidemia, atherosclerosis, and hypersensitive inflammatory response. Rev-erbs (including Rev-erbα and Rev-erbβ) are also involved in dyslipidemia. In addition, the NR4A family (including Nurr1, Nur11, and NOR-1) is thought to be involved in obesity, energy balance, homeostasis, lipid utilization, and lipid and carbohydrate homeostasis. Based on the disclosures herein in combination with the state of the art, one of skill in the art will recognize which orphan nuclear receptor protein, orphan nuclear receptor-modulating nucleic acid, or orphan nuclear receptor agonist or antagonist, may be administered in conjunction with the methods and compositions herein, in order to effectively treat an orphan nuclear receptor-mediated disease.

In certain embodiments the compositions and methods herein may be used to treat a disease or disorder involving dysfunction of factors controlling chromatin modification, and the conjugate is transported into cells in which altered chromatin modification state is desired. In certain embodiments, the chromatin modification factors are histone deacetylases, histone methyltransferases, histone kinases, histone phosphatases, histone ubiquitinylating enzymes, or histone poly-ADP-ribosylases. Also, chromatin assembly factors and nucleosome remodeling factors (and nucleic acids modulating their expression) may be administered. In certain embodiments, DNA methyltransferases (such as DNMT1, DNMT2, DNMT3) or nucleic acids modulating their expression may be administered in order to treat diseases associated with altered DNA methyltransferase function, such as ICF Syndrome.

In certain embodiments, the disease or disorder involves incorrect hormone levels. The hormone levels may be inappropriately high or low. If the disease is associated with low hormone levels, one may administer a gene (or gene product) in the synthesis pathway for that hormone. For example, to treat low testosterone levels, a gene or gene product of 17β hydroxysteroid dehydrogenase, 3β hydroxysteroid dehydrogenase, or 17,20 lyase may be administered. Alternatively, if the disease is associated with elevated hormone levels, a nucleic acid (such as a siRNA) designed to reduce levels of the hormone synthesis pathway components may be administered. Hormones include testosterone, estrogen, estradiol, and progesterone.

In certain embodiments, the methods herein may be used to target therapeutic antibodies, or nucleic acids encoding them, to particular target cells. The antibodies may be, for example, monoclonal antibodies, polyclonal antibodies, single-chain antibodies, or bispecific antibodies. Suitable therapeutic antibodies include, but are not limited to, Anti_EGFr antibodies (e.g., panitumamab, Erbitux (cetuximab), matuzumab, IMC-IIF 8, TheraCIM hR3), denosumab, Avastin (bevacizumab), Anti-HGF antibodies, Humira (adalimumab), Anti-Ang-2 antibodies, Herceptin (trastuzumab), Remicade (infliximab), Anti-CD20 antibodies, rituximab, Synagis (palivizumab), Mylotarg (gemtuzumab oxogamicin), Raptiva (efalizumab), Tysabri (natalizumab), Zenapax (dacliximab), NeutroSpec (Technetium (.sup.99 mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, and natalizumab.

In certain embodiments, the therapeutic agent is a proteasome inhibitor. Proteasome inhibitors may be used, for example, in the treatment of infectious diseases like HIV/AIDS and Hepatitis C, and for cancer therapy. In certain embodiments, the protease inhibitor is an antibody that binds a protease.

In certain embodiments, the subject conjugates can be used to deliver an expression construct to cells, such as muscle cells, that encodes a therapeutic protein. For instance, the expression construct can encode a therapeutic protein that is secreted by the transduced cell. For example, the expression construct acid can encode an angiogenic growth factor such as VEGF, a fibroblast growth factor such as basic FGF or FGF-4, placental growth factor, hepatocyte growth factor, angiogenin, angiopoietin-1, pleiotrophin, transforming growth factor (α or β), or tumor necrosis factor α The expression construct also can encode a natiuretic peptide such as an atrial natiuretic peptide (ANP) or a brain natriuretic peptide (BNP), prostacyclin synthase, nitric oxide synthase, angiostatin, endostatin, erythropoietin (EPO), blood factors (such as coagulation factors like Factor I, II, III, IV, V, VII, VIII, IV, X, XI, XII and XIII), GM-CSF, or an interleukin such as IL-1,2,3, 4, 5, 6, 7, 8, 9, 10, 11, 12, 13, 14, 15, 16, 17, or 18. The expression construct can encode an adhesion molecule such as a selectin (e.g., E, L, or P selectin), an extracellular matrix protein (e.g., collagen type I, III, or IV; fibronectin; laminin; or vitronectin), an integrin (e.g., $\alpha_5 \beta_1$), or an intracellular adhesion molecule such as ICAM or a vascular cell adhesion molecule (VCAM).

In either case, the expression construct that is delivered typically is part of a vector in which a regulatory element such as a promoter is operably linked to the nucleic acid of interest. The promoter can be constitutive or inducible. Non-limiting examples of constitutive promoters include cytomegalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus. The inducer also can be an illumination agent such as light and light's various aspects, which include wavelength, intensity, fluorescence, direction, and duration.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory elements that may be useful in vectors, include, but are not limited to, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a nucleic acid construct as desired to obtain optimal expression of the nucleic acids in the cell(s). Sufficient expression, however, may sometimes be obtained without such additional elements.

Vectors also can include other elements. For example, a vector can include a nucleic acid that encodes a signal peptide such that the encoded polypeptide is directed to a particular cellular location (e.g., a signal secretion sequence to cause the protein to be secreted by the cell) or a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

Viral vectors can be used to form the conjugates, and include adenovirus, adeno-associated virus (AAV), retroviruses, lentiviruses, vaccinia virus, measles viruses, herpes viruses, and bovine papilloma virus vectors (see, Kay et al., Proc. Natl. Acad. Sci. USA 94:12744-12746 (1997) for a review of viral and non-viral vectors). Viral vectors are modified so the native tropism and pathogenicity of the virus has been altered or removed. The genome of a virus also can be modified to increase its infectivity and to accommodate packaging of the nucleic acid encoding the polypeptide of interest.

Non-viral vectors can also be used in the subject conjugates. To further illustrate, in one embodiment, the mammalian serum protein that is encoded by the vector is selected from the group consisting of a tissue-type plasminogen activator, a receptor of a tissue-type plasminogen activator, a streptokinase, a staphylokinase, a urokinase, and coagulation factors. The invention also provides a method for treating associated with the formation of clots in its circulation, including the step of administering to the mammal a conjugate that causes the recombinant expression and secretion into the blood, such as from transduced muscle cells, of a therapeutically effective amount of such a mammalian serum protein.

In another embodiment, the mammalian serum protein is glucocerebrosidase. The invention also provides a method of treating a patient having Gaucher disease, including the step of administering to the patient a conjugate that causes the recombinant expression and secretion into the blood, such as from transduced muscle cells, of a therapeutically effective amount of glucocerebrosidase.

In still another embodiment, the mammalian serum protein is α-galactosidase A. The invention also provides a method of treating a mammal having Fabry disease, including the step of administering to the patient a conjugate that causes the recombinant expression and secretion into the blood, such as from transduced muscle cells, of a therapeutically effective amount of α-galactosidase A.

In still another embodiment, the mammalian serum protein is a cytokine. The cytokine can be selected from the group consisting of IFN-α, IFN-β, IFN-γ, IL-2, IL-3, IL-4, IL-5, IL-6, IL-7, IL-8, IL-9, IL-10, IL-12 and IL-15. The invention also provides a method of treating a mammal having cancer or a bacterial or viral infection, including the step of administering to the mammal a conjugate that causes the recombinant expression and secretion into the blood, such as from transduced muscle cells, of a therapeutically effective amount of such a cytokine.

In still another embodiment, the mammalian serum protein is a peptide hormone. The peptide hormone can be selected from the group consisting of antimullerian hormone (AMH), adiponectin, adrenocorticotropic hormone (ACTH), angiotensinogen and angiotensin, antidiuretic hormone (ADH), atrial-natriuretic peptide (ANP), calcitonin, cholecystokinin (CCK), corticotropin-releasing hormone (CRH), erythropoietin (EPO), follicle stimulating hormone (FSH), gastrin, glucagon, gonadotropin-releasing hormone (GnRH), growth hormone-releasing hormone (GHRH), human chorionic gonadotropin (hCG), growth hormone (GH), insulin, insulin-like growth factor (IGF), leptin, luteinizing hormone (LH), melanocyte stimulating hormone (MSH or α-MSH), neuropeptide Y, oxytocin, parathyroid hormone (PTH), prolactin (PRL), relaxin, renin, secretin, somatostatin, thrombopoietin, thyroid-stimulating hormone (TSH), and thyrotropin-releasing hormone (TRH). The invention also provides a method for hormone replacement therapy in a mammal, including the step of administering to the mammal a conjugate that causes the recombinant expression and secretion into the blood, such as from transduced muscle cells, of a therapeutically effective amount of such a peptide hormone.

In still other embodiments, the subject conjugate can be selected to include an expression vector that causes the recombinant expression and secretion into the blood, such as from transduced muscle cells, of an enzyme selected from the group consisting of L-asparagine, L-glutaminase-L-asparaginase, L-methioninase, L-phenylalanine, ammonialyase, L-arginase, L-tyrosinase, L-serine dehydratase, L-threonine deaminase, indolyl-3-alkane hydroxylase, neuraminidase, ribonuclease, a protease, pepsin, and a carboxypeptidase. Such constructs can be used as part of a treatment program for cancer.

In another embodiment, the subject conjugate can be selected to include an expression vector that causes the recombinant expression and secretion into the blood of lysostaphin. The invention also provides a method of treating a mammal having a bacterial infection, including the step of administering such a conjugate.

In certain embodiments, the subject methods and compositions are used to deliver a prodrug of any of the drugs listed herein.

Pharmaceutical compositions including a disclosed conjugate may be used in the methods described herein. Thus, in one embodiment, a pharmaceutical composition including a conjugate present in an amount effective to treat a disease or disorder affecting a tissue expressing a nucleoside transport pathway in a subject is used in methods described herein. In another embodiment, a pharmaceutical composition including a conjugate present in an amount effective to treat a disease or disorder of skeletal muscle in a subject is used in methods described herein. In addition to the conjugate, the pharmaceutical composition may also contain other therapeutic agents, and may be formulated, for example, by employing conventional vehicles or diluents, as well as pharmaceutical additives of a type appropriate to the mode of desired administration (for example, excipients, preservatives, etc.) according to techniques known in the art of pharmaceutical formulation.

In certain embodiments, the compositions disclosed herein are formulated with additional agents that promote entry into the desired cell or tissue. Such additional agents include micelles, liposomes, and dendrimers.

The term "effective amount" of an active agent refers an amount that is non-toxic to a subject or a majority or normal cells, but is an amount of the active agent that is sufficient to provide a desired effect (e.g., treatment of a skeletal muscle disorder, metabolic disorder, blood disorder, or cancer). This amount may vary from subject to subject, depending on the species, age, and physical condition of the subject, the severity of the disease that is being treated, the particular conjugate, or more specifically, the particular active agent used, its mode of administration, and the like. Therefore, it is difficult to generalize an exact "effective amount," yet, a suitable effective amount may be determined by one of ordinary skill in the art.

The term "pharmaceutically acceptable" refers to the fact that the carrier, diluent or excipient must be compatible with the other ingredients of the formulation and not deleterious to the recipient thereof. For example, the carrier, diluent, or excipient or composition thereof may be administered to a subject along with a conjugate of the invention without causing any undesirable biological effects or interacting in an undesirable manner with any of the other components of the pharmaceutical composition in which it is contained.

Pharmaceutical compositions including the conjugate may be administered by any suitable means, for example, parenterally, such as by subcutaneous, intravenous, intramuscular, intrathecal, or intracisternal injection or infusion techniques (e.g., as sterile injectable aqueous or non-aqueous solutions or suspensions) in dosage formulations containing non-toxic, pharmaceutically acceptable vehicles or diluents. In certain embodiments the conjugate is administered parenterally, or more preferably, intravenously.

The mode of delivery chosen for administration of conjugates according to the present invention to a subject, such as a human patient or mammalian animal, will depend in large part on the particular active agent present in the conjugate and the target cells. In general, the same dosages and administration routes used to administer the active agent alone will also be used as the starting point for the conjugate. However, it is preferred that smaller doses be used initially due to the expected increase in cellular penetration of the active agent. The actual final dosage for a given route of administration is easily determined by routine experimentation. In general the same procedures and protocols that have been previously used for other antibody-based targeting conjugates (e.g., parenterally, intravenous, intrathecal, and the like) are also suitable for the conjugates of the present invention.

The pharmaceutical compositions of the conjugate can be administered either alone or in combination with other therapeutic agents, may conveniently be presented in unit dose form and may be prepared by any of the methods well known in the art of pharmacy. All methods include bringing the conjugate into association with the carrier, which constitutes one or more accessory ingredients. In general, the pharmaceutical compositions are prepared by uniformly and intimately bringing the active ingredient into association with a liquid carrier. In a pharmaceutical composition, the conjugate is included in an amount sufficient to produce the desired effect upon the process or condition of disease.

Depending on the condition being treated, these pharmaceutical compositions may be formulated and administered systemically or locally. Techniques for formulation and administration are generally known in the art. Suitable routes may, for example, parenteral delivery, including intramuscular, subcutaneous, intramedullary, intrathecal, intraventricular, intravenous, or intraperitoneal. For injection, the pharmaceutical compositions of the invention may be formulated in aqueous solutions, preferably in physiologically compatible buffers such as Hanks' solution, Ringer's solution, or physiologically buffered saline.

The present disclosure also provides a pharmaceutical composition including a conjugate described herein and an agent that promotes ENT2 expression in a tissue. In some aspects, the agent that promotes ENT2 expression in a tissue is an agent that inhibits hypoxia or an agent that inhibits HIF-1. The tissue may be a hypoxic tissue, such as a hypoxic tumor, a tissue with insufficient vasculature, an ulcer, a diabetic ulcer, a poorly-healing wound, an ischemic area, an ischemic area resulting from stroke, or an ischemic area resulting from cardiovascular disease. In certain embodiments, the agent that inhibits HIF-1α is a siRNA, an RNAi construct, a hairpin RNA, or a miRNA that reduces HIF-1α expression. In some embodiments, the HIF-1α inhibitor is a chemotherapeutic drug, topotecan, NSC 644221, PX-478, YC-1,17-AAG, or bevacizumab. In certain embodiments, the agent that inhibits hypoxia is an agent that normalizes tumor vasculature, or an agent that alters the redox state of a tissue. The agent that inhibits hypoxia may be excess oxygen, TSC, or almitrine. Excess oxygen may be delivered, for example, by intubation, an oxygen mask, or a hyperbaric chamber. In certain embodiments, the agent that promotes ENT2 expression is an inhibitor of a gene that downregulates ENT2, such as HIF-1α. In other embodiments, the agent that promotes ENT2 expression is a nucleic acid encoding ENT2, for example an expression construct that drives expression of ENT2 or any fragment thereof having essentially the same therapeutic transport activity as full-length ENT2.

Furthermore, herein is provided a method of treating an ENT-2 deficient tissue, wherein the method includes: a) administering an agent that promotes ENT2 expression and/or activity, and b) administering one of the conjugates disclosed herein.

In certain aspects, a conjugate as described herein may be administered together with ATP or an ATP-generating agent. These agents may be used to inhibit hypoxia and/or ischemia In certain aspects, ATP is specifically delivered to the target tissue, for example, using liposomes. Methods of delivering ATP to ischemic tissue are known in the art, and are described in U.S. Pat. No. 7,056,529 and Verma et al. (J Control Release 108(2-3): 460-471 (2005)).

In certain embodiments, a patient is treated with a hypoxia-inhibiting agent and a conjugate herein prior to surgery, as a prophylactic treatment for ischemia caused by surgery.

A number of drugs affect tumor vasculature. While the mechanism of such drugs is not fully understood, there appear to be three broad classes of vasculature-targeting agents. First, an agent may be anti-angiogenic. Such agents prevent the growth of new blood vessels, starving the tumor of blood and oxygen. Such agents make a tumor more hypoxic. Second, an agent may collapse pre-existing tumor vasculature, also increasing the hypoxia of the tumor. Third, vasculature-normalizing agents reduce the abnormalities of the tumor vasculature. For example, they may reduce the number of excess epithelial cells in the tumor vasculature. These agents improve blood flow to the tumor and reduce hypoxia. Paradoxically, vasculature-normalizing agents may be used to impede tumor growth, by allowing other therapeutic molecules (such as chemotherapeutic drugs) better access to the tumor.

Some therapies previously thought to be anti-angiogenic may instead produce vasculature normalization. For example, one may block vascular endothelial growth factor (VEGF) or its receptor (VEGFR2), causing apoptosis of endothelial cells. Consequently there is a decrease in blood vessel diameter, density and permeability. There is also a decrease in interstitial fluid pressure and, at least in some instances, elevated oxygen tension (reviewed in Jain R et al., Nature Medicine 7:987-989 (2001)). Various other therapeutics also contribute to vasculature normalization, including ST1571, C225, and Herceptin™, which block PDGFR, HER1 and HER2 signaling, respectively.

Therapeutic antibodies may be used to normalize tumor vasculature. For example, a neutralizing antibody (A4.6.1) against VEGF/VPF is described in Yuan et al. (Proc Natl Acad Sci USA 93(25):14765-70 (1996)). Permeabolization of the tumor vasculature was observed a few hours after injection and lasted about 5 days. Also, the (VEGFR)-2 neutralizing antibody DC101 may be used to normalize tumor vasculature as described in Kadambi et al. (Cancer Res. 61(6):2404-8 (2001)). Humanized versions of these antibodies, and antibody variants such as single-chain antibodies, may be used in accordance with the methods disclosed herein.

The invention will now be described in greater detail by reference to the following non-limiting examples.

EXAMPLE 1

Increased Solubility and Secretion of Peptide Conjugates

This example illustrates generation and purification of a peptide conjugate of the present invention produced in *Pichia pastoris* X-33 cells.

Plasmid constructs for expression of a peptide conjugate including 3E10 Fv in the X-33 strain of *Pichia pastoris*, was generated by ligating cDNA encoding the single-chain Fv fragment of mAb 3E10 into pPicZαA, as previously described (Weisbart et al., Cancer Lett. 195:211-9 (2003); and Weisbart et al., Int J Oncol 25:1113-8 (2004)). The first construct, pPicZαA-AGIH-Fv-HSP70, generates the following peptide conjugate: peptide(AGIH)-antibody(3E10 FV)-biologically active molecule (HSP70). The second construct, pPicZαA-Fv-HSP70, generates a similar peptide conjugate except without the N-terminal peptide having amino acid sequence AGIH (SEQ ID NO: 8).

Peptide conjugates were generated by transfecting *Pichia pastoris* X-33 cells with pPicZαA-Fv-HSP70 and pPicZαA-AGIH-Fv-HSP70.

In order to analyze the ability of the AGIH peptide to provide increased secretion and solubility as compared to a conjugate not including AGIH, secreted peptide conjugates containing a $HIS_6$ (SEQ ID NO 9) tag were concentrated and isolated by IMAC on Ni-NTA agarose. Purified proteins were analyzed by SDS-PAGE in 4-20% gradient gels and stained with GelCode Blue™.

Fv-HSP70 in the absence of AGIH was identified as a band of about 106 kDa as expected (data not shown) and as confirmed by Western blot analysis. Fv-HSP70 formed large aggregates at 150 kDa as confirmed by Western blot. In sharp contrast, AGIH-Fv-HSP70 was free of aggregates. These results are consistent with increased solubility of Fv-HSP70 containing the N-terminal amino acid sequence AGIH (SEQ ID NO: 8).

In addition to increasing secretion and solubility of Fv-HSP70, the inventors have shown that the AGIH amino-terminal sequence improves the secretion of 3E10 Fv alone and increases secretion of three bispecific single chain Fvs produced as molecular fusion proteins with mAb 3E10 Fv. mAb 3E10 with C-terminal myc-$His_6$ tags was produced in *Pichia pastoris* X-33 cells as an Fv fragment with and without AGIH as N-terminal amino acids. The Fv fragments were purified on Ni-NTA columns and eluted with imidazole. Comparable aliquots were analyzed by SDS-PAGE, transblotted to nitrocellulose and developed by Western blot with antibodies to the C-terminal myc tag.

The addition of the four ammo acids AGIH (SEQ ID NO: 8) to the N-terminus of mAb 3E10 Fv fragment markedly enhanced secretion from *Pichia pastoris* and markedly improved solubility of the secreted Fv fragment as determined from the quantity of protein based on the bands noted above. There was a large increase in AGIH-Fv compared to Fv without AGIH N-terminal amino acids. The Fv fragment was modified by adding nucleosides to Fv-cDNA by PCR with the use of a primer that encoded nucleosides corresponding to the desired amino acid sequences.

Although the invention has been described with reference to the above example, it will be understood that modifications and variations are encompassed within the spirit and scope of the invention. Accordingly, the invention is limited only by the following claims.

What is claimed is:

1. A peptide-antibody conjugate comprising,
a peptide of about 4 to 50 amino acid residues comprising the amino acid sequence AGIH (SEQ ID NO: 8); and
mAb 3E10, or functional fragment thereof, having a binding specificity as produced by a hybridoma having ATCC accession number PTA 2439, wherein the peptide is conjugated to the N-terminus of the antibody or functional fragment thereof.

2. The conjugate of claim 1, wherein the functional fragment is selected from the group consisting of Fab, F(ab')$_2$, Fv, and single chain Fv (scFv) fragments.

3. The conjugate of claim 1, wherein the functional fragment is an scFv fragment of mAb 3E10.

4. The conjugate of claim 1, wherein the functional fragment comprises the variable region of the heavy chain (VH) and variable region of the kappa light chain (Vκ) of mAb 3E10.

5. The conjugate of claim 4, wherein the antigen-binding portion of mAb 3E10 further comprises the signal peptide of the Vκ.

6. The conjugate of claim 1, wherein the peptide is joined to the antibody by a linker molecule.

7. The conjugate of claim 1, wherein the conjugate is a genetic fusion.

8. The conjugate of claim 1, wherein the conjugate further includes an additional biologically active molecule, wherein the biologically active molecule is a nucleic acid sequence or a protein.

9. The conjugate of claim 8, wherein the additional biologically active molecule is selected from the group consisting of an antibody, an antibody fragment, an enzyme, a transcription factor, an siRNA molecule, a DNA molecule, an RNA molecule, an siRNA-protein conjugate, an siRNA-peptide conjugate, and siRNA-antibody conjugate.

10. The conjugate of claim 9, wherein the additional biologically active molecule comprises an antibody fragment selected from the group consisting of a Fab fragment, a F(ab)2 fragment, an FV fragment, a single chain FV (scFV) fragment, a dsFV fragment, and a dimeric scFV.

11. The conjugate of claim 9, wherein the additional biologically active molecule comprises an antibody selected from the group consisting of a chimeric antibody, a humanized antibody, a CDR-grafted antibody, a bifunctional antibody, a single chain antibody, and an antibody polypeptide dimer.

12. The conjugate of claim 8, wherein the additional biologically active molecule is HSP70.

13. The conjugate of claim 8, wherein the peptide-antibody conjugate is joined to the additional biologically active molecule by a linker molecule.

14. The conjugate of claim 8, wherein the biologically active molecule is a protein and the conjugate is a genetic fusion.

* * * * *